United States Patent [19]

Ogawa et al.

[11] Patent Number: 5,202,464
[45] Date of Patent: Apr. 13, 1993

[54] OPTICALLY ACTIVE AMINOCYCLITOLS

[75] Inventors: Seiichiro Ogawa; Akihiro Isaka, both of Tokyo; Kunio Kageyama, Yokohama; Morihisa Machida, Kanagawa, all of Japan

[73] Assignee: The Yokohama Rubber Co., Ltd., Tokyo, Japan

[21] Appl. No.: 684,334

[22] Filed: Apr. 12, 1991

[30] Foreign Application Priority Data

| Apr. 16, 1990 | [JP] | Japan | 2-99802 |
| Apr. 16, 1990 | [JP] | Japan | 2-99803 |
| Apr. 16, 1990 | [JP] | Japan | 2-99804 |
| Apr. 16, 1990 | [JP] | Japan | 2-99805 |
| Apr. 16, 1990 | [JP] | Japan | 2-99806 |
| Jun. 7, 1990  | [JP] | Japan | 2-149452 |

[51] Int. Cl.$^5$ .............................................. C07C 67/02
[52] U.S. Cl. ....................................... 560/250; 560/251
[58] Field of Search ................................. 560/250, 251

[56] References Cited

U.S. PATENT DOCUMENTS 4,906,761  3/1990  Billington ........................ 549/360

OTHER PUBLICATIONS

Kurihara et al., "Chemistry of Benzeneglycols: Part XVII, A New Synthesis of Streptamine", Agr. Biol. Chem. 31:1166-1170 (1967).
"Chemistry Letters (1985)", S. Ogawa et al., p. 1581.
"Liebigs Ann. Chem. (1981)", H. Paulsen et al., pp. 2180-2203.
"Liebigs Ann. Chem. 689 (1965)", M. Nakajima et al., pp. 243-247.
"Newer Methods of Preparative Organic Chemistry", F. W. Lichtenthaler, vol. IV, (1968), p. 155.
"J. Syn. Org. Chem., Japan", 27, (1969), S. Ogawa, pp. 731-746.

Primary Examiner—Jose G. Dees
Assistant Examiner—Joseph Conrad III
Attorney, Agent, or Firm—Finnegan, Henderson, Farabow, Garrett & Dunner

[57] ABSTRACT

Inositol compounds grouped into an aminocyclitol family are disclosed which have stereospecific structure and optical activity and find application to the manufacture of medicinal products and agricultural chemicals. The compound is produced with use of optically active L-quebrachitol as a starting material and by way of specific steps of reaction.

16 Claims, 11 Drawing Sheets

OPTICALLY ACTIVE AMINOCYCLITOLS

BACKGROUND OF THE INVENTION

1. Field of the Invention

This invention relates to aminocyclitols having stereospecific structure and optical activity and further to a process for their production. The above compounds are suitable particularly for use as starting materials in the preparation of medicinal products such as antibiotics and anticarcinogens and of agricultural chemicals.

2. Description of the Prior Art

Aminocyclitols, also termed aminosaccharides, are compounds obtained by rearranging a cyclic alcohol to have amino groups substituted for the hydroxyl groups. These compounds have gained a high reputation since streptamine, one member of the aminocyclitol family, was discovered to be a key component for streptomycin. Several other members of this family are currently applicable to certain antibiotics. Furthermore, the aminocyclitol compounds serve to construct glycoconjugates which occur naturally widely as polysaccharides and have a biologically important role to maintain the life of animals.

Aminocyclitols, from the standpoint of their unique significant function, have been synthesized with various chemical modes of reaction. One such mode is disclosed by S. Ogawa et al., Chem. Lett., 1518 (1985) in which an aminosaccharide is prepared by reacting furan with acrylic acid through the Diels-Alder procedure, thereby forming 1,4-anhydrocyclohexane, and subsequently by decomposing the same with acetic acid to open the anhydro ring, followed by azidation, reduction and other necessary treatments. It is known from H. Paulsen et al., Liebigs Ann. Chem., 2180–2203 (1981) that valienamine of optical activity can be derived via 21 steps of reaction from L-quebrachitol of natural origin. Benzene glycol is employed as a starting material in an aminocyclitol synthesis of M. Nakajima et al., Liebig Ann. Chem., 689, 243 (1965). A disulfonate or cis-1,4-diepoxide derivative of an inositol is reacted with hydrazine as reported by F. W. Lichtenthaler, "Newer Methods of Preparative Organic Chemistry", IV, 155 (1968) and by S. Ogawa, J. Syn. Org. Chem., Japan, 27, 731 (1969).

The foregoing aminocyclitol syntheses of the prior art, however, have a drawback in that they involve numerous complicated reaction steps including in most cases a tedious optical resolution step and entail low product yield.

SUMMARY OF THE INVENTION

The present invention seeks to provide novel, stereospecific, optically active aminocyclitols. The invention also seeks to provide a process for the production of these compounds which enables operation with a total of reaction steps held to an absolute minimum and with an adverse route of optical resolution omitted, thus contributing to utmost efficiency and high productivity.

Many other objectives and advantages of the invention will be better understood from the following description taken in conjunction with the accompanying drawings. Like reference numerals refer to like or corresponding compounds throughout the several views.

More specifically, one aspect of the invention provides an inositol compound having stereospecific structure and optical activity in a chiro, muco, scyllo, allo, neo or myo type.

Another aspect of the invention provides a process for the production of an inositol compound having stereospecific structure and optical activity, the process comprising the steps of aziding L-quebrachitol as a starting material at one or more preselected hydroxyl groups thereof and thereafter reducing and acetylating the resulting azido groups, and acetylating the remaining hydroxyl groups of the starting material.

DETAILED DESCRIPTION OF THE INVENTION

Figure 1:
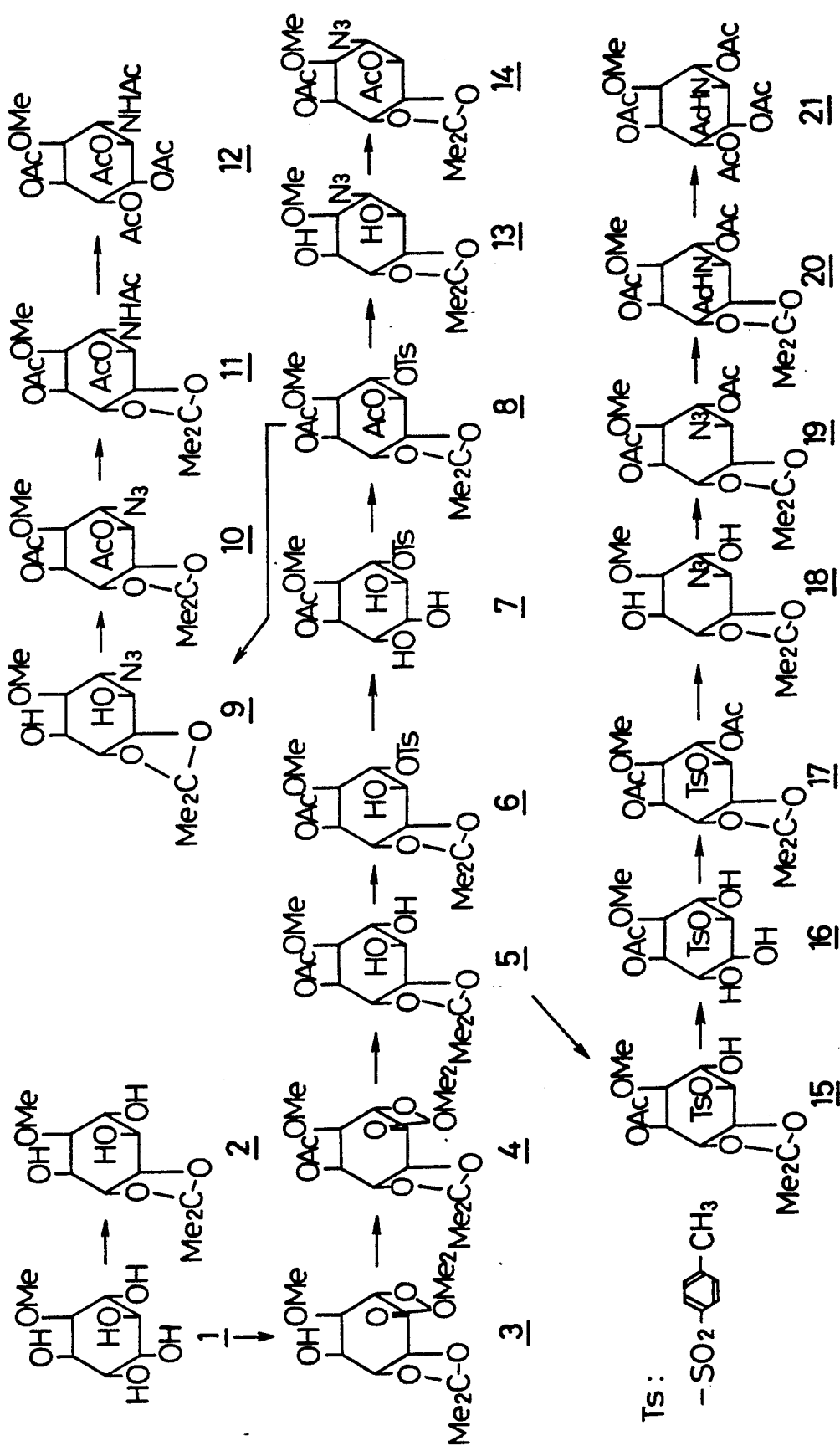
FIG. 1, FIGS. 2A and 2B, FIGS. 3 to 5 and FIGS. 6A to 6E are schematic views of the sequences of reaction embodying the process of the present invention and showing the routes from a specific starting material to the respective final compounds.

The following inositol compounds, compounds A to O, are provided in accordance with the present invention. They are generally grouped into an aminocyclitol family and physicochemically characterized as given below along with the structural formulae.

Compound A 1L-3-acetamido-1,4,5,6-tetra-O-acetyl-3-deoxy-2-O-methyl-chiro-inositol

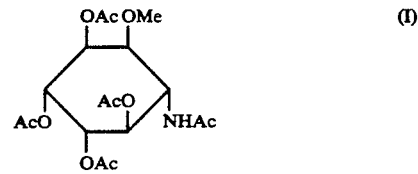

(I)

appearance: white solid.
mp: 187°–188° C.
$[\alpha]_D^{21}$: −13.9°]C.
solubility: insoluble in hydrocarbon solvents but soluble in alcohols, hydrogenated hydrocarbons, dimethylformaldehyde and the like.

Compound B 1L-3-acetamido-1,2,4,6-tetra-O-acetyl-3-deoxy-5-O-methyl-chiro-inositol

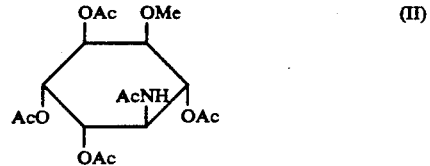

(II)

appearance: white solid.
mp: 157°–158° C.
$[\alpha]_D^{21}$: −11.9°.
solubility: similar to that of compound A.

Compound C 1D-2-acetamido-1,3,4,5-tetra-O-acetyl-2-deoxy-6-O-methyl-chiro-inositol -continued

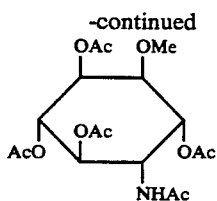
(III)

appearance: colorless syrup.
$[\alpha]_D^{21}$: +33.9°.
solubility: similar to that of compound A.

Compound D 1L-2-acetamido-1,3,4,6-tetra-O-acetyl-2-deoxy-5-O-methyl-chiro-inositol

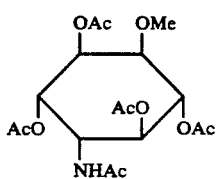
(IV)

appearance: white crystal.
mp: 193°–194° C.
$[\alpha]_D^{23}$: −33.2°.
solubility: similar to that of compound A.

Compound E 1D-2,4-diacetamido-1,3,5-tri-O-acetyl-2,4-dideoxy-6-O-methyl-chiro-inositol

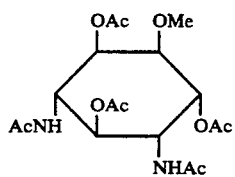
(V)

appearance: white crystal.
mp: 243°–245° C.
$[\alpha]_D^{24}$: +25.4°.

Compound F 1D-1,2-diacetamido-4,5,6-tri-O-acetyl-1,2-dideoxy-3-O-methyl-chiro-inositol

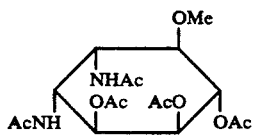
(VI)

appearance: white crystal.
mp: 137°–140° C.
$[\alpha]_D^{24}$: +17.1°.
solubility: similar to that of compound A.

Compound G 1L-3-acetamido-1,2,4,6-tetra-O-acetyl-3-deoxy-5-O-methyl-muco-inositol -continued

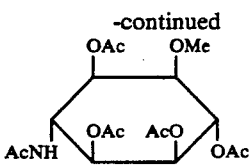
(VII)

appearance: white crystal.
mp: 161°–162° C.
$[\alpha]_D^{21}$: +5.4°.
solubility: similar to that of compound A.

Compound H 1L-1-acetamido-2,3,4,6-tetra-O-acetyl-1-deoxy-5-O-methyl-chiro-inositol

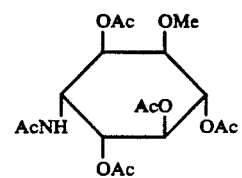
(VIII)

appearance: syrup.
$[\alpha]_D^{32}$: −9°.
solubility: similar to that of compound A.

Compound I 1D-1-acetamido-3,4,5,6-tetra-O-acetyl-1-deoxy-2-O-methyl-scyllo-inositol

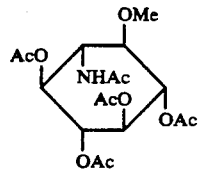
(IX)

appearance: white solid.
mp: 215°–216° C.
$[\alpha]_D^{21}$: +13.5°.
solubility: similar to that of compound A.

Compound J 1L-1-acetamido-3,4,5,6-tetra-O-acetyl-1-deoxy-2-O-methyl-chiro-inositol

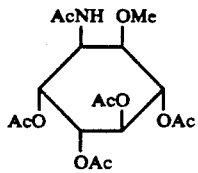
(X)

appearance: white solid.
mp: 183°–184° C.
$[\alpha]_D^{21}$: −10.5°.
solubility: similar to that of compound A.

Compound K 1L-1-acetamido-2,4,5,6-tetra-O-acetyl-1-deoxy-3-O-methyl-scyllo-inositol

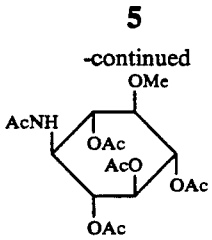

appearance: white solid.
mp: 206°–208° C.
$[\alpha]_D^{21}$: −3.4°.
solubility: similar to that of compound A.

Compound L 1D-2-acetamido-1,4,5,6-tetra-O-acetyl-2-deoxy-3-O-methyl-allo-inositol

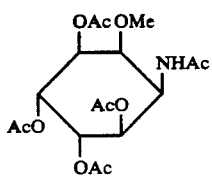

appearance: syrup.
$[\alpha]_D^{20}$: +8.5°.
solubility: similar to that of compound A.

Compound M 1D-1-acetamido-2,3,4,6-tetra-O-acetyl-1-deoxy-5-O-methyl-neo-inositol

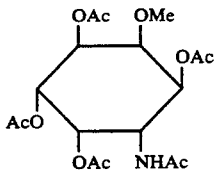

appearance: white solid.
mp: 270°–280° C.
$[\alpha]_D^{20}$: +2.7°.
solubility: similar to that of compound A.

Compound N 1D-3-acetamido-1,2,4,5-tetra-O-acetyl-3-deoxy-6-O-methyl-chiro-inositol

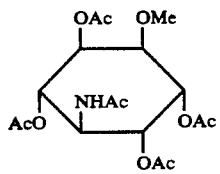

appearance: white solid.
mp: 144°–145° C.
$[\alpha]_D^{19}$: +14.6°.
solubility: similar to that of compound A.

Compound O 1L-1-acetamido-2,3,4,5-tetra-O-acetyl-1-deoxy-6-O-methyl-myo-inositol

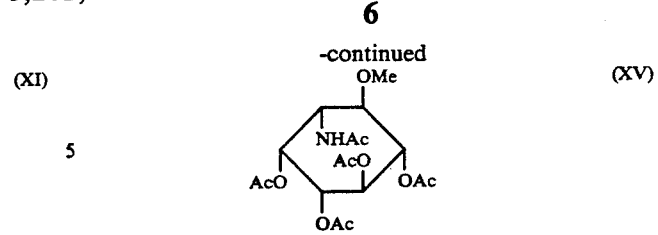

appearance: white solid.
mp: 189°–190° C.
$[\alpha]_D^{20}$: +8.9°.
solubility: similar to that of compound A.

Compounds A to O have optical activity as their production relies, according to one important aspect of the invention, upon the use of optically active L-quebrachitol as a starting material. Such compounds may, where desired, be converted into their analogs or derivatives to suit particular application for medicinal and agricultural purposes.

L-Quebrachitol eligible for purposes of the invention is an inositol monomethyl ether that is L-(-)2-O-methyl-chiro-inositol. It finds a source of supply from quebraco barks, Hevea brasiliensis or para rubber trees and various other plants.

L-Quebrachitol according to the invention may be easily available from serums as disclosed for instance in JP-A 2-193332. The serum is a byproduct left upon coagulation and removal of substantially all rubber components from a natural rubber latex. The byproduct is treated concentrate or particulate and dissolved in methanol, followed by concentration of the solution. Thus a quebrachitol is obtained in crystalline form. All such quebrachitols are of an optically active, levorotary nature.

In implementing the process of the invention, L-quebrachitol should follow certain specific sequences of reaction so as to produce compounds A to O. The process essentially comprises the steps of aziding the starting material at one or more preselected positions and thereafter reducing and acetylating the resulting azido groups, and acetylating the remaining hydroxyl groups. Described here and below are the positions of L-quebrachitol to be azided (a) and the positions of hydroxyl groups to be acetylated (b) with respect to each of compounds A to O.

| | |
|---|---|
| Compound A: | (a) - 3 position |
| | (b) - 1, 4, 5 and 6 positions |
| Compound B: | (a) - 4 position |
| | (b) - 1, 3, 5 and 6 positions |
| Compound C: | (a) - 4 position |
| | (b) - 1, 3, 5 and 6 positions |
| Compound D: | (a) - 5 position |
| | (b) - 1, 3, 4 and 6 positions |
| Compound E: | (a) - 4 and 6 positions |
| | (b) - 1, 3 and 5 positions |
| Compound F: | (a) - 1 and 6 positions |
| | (b) - 3, 4 and 5 positions |
| Compound G: | (a) - 6 position |
| | (b) - 1, 3, 4 and 5 positions |
| Compound H: | (a) - 6 position |
| | (b) - 1, 3, 4 and 5 positions |
| Compound I: | (a) - 1 position |
| | (b) - 3, 4, 5 and 6 positions |
| Compound J: | (a) - 1 position |
| | (b) - 3, 4, 5 and 6 positions |
| Compound K: | (a) - 6 position |
| | (b) - 1, 3, 4 and 5 positions |
| Compound L: | (a) - 3 position |
| | (b) - 1, 4, 5 and 6 positions |
| Compound M: | (a) - 4 position |

| | -continued | |
|---|---|---|
| | (b) - 1, 3, 5 and 6 positions | |
| Compound N: | (a) - 5 position | |
| | (b) - 1, 3, 4 and 6 positions | |
| Compound O: | (a) - 1 position | |
| | (b) - 3, 4, 5 and 6 positions | |

Referring now to the drawings, FIG. 1 illustrates a first preferred embodiment of the process of the invention for producing compounds A and B.

A starting material or L-quebrachitol 1 has at the 2-position a methoxy group resulting from methyl etherification and at the 3- and 4-position and at the 5- and 6-position two adjoining pairs of hydroxyl groups. The paired hydroxyl groups are selectively subjected to protection with a suitable protective group of a bridging type such as an isopropylidene, cyclohexylidene or benzylidene group or the like. The protective group may be introduced with use of 2,2-dimethoxypropane or acetone, cyclohexanone or benzaldehyde.

Compound 1 is treated with a given compound, with 2,2-dimethoxypropane in FIG. 1, thereby forming a mixture of compound 2 in which one paired hydroxyl group has been masked with a protective group, with an isopropylidene group in FIG. 1, only at the 5- and 6-position and compound 3 in which two paired hydroxyl groups have been masked with a similar protective group both at the 3- and 4-position and at the 5- and 6-position. Compound 3 is isolated by extraction of the mixture with an organic solvent such as ethyl acetate, followed by reaction with acetic anhydride in the presence of pyridine, so that compound 4 is yielded which has been derived from acetylation of the single hydroxyl group located in compound 3 at the 1-position. Compound 4 when treated for example with acetic acid of about 60 to 80% in concentration is rendered free from protection at the 3- and 4-position and thus converted to compound 5.

Compound 5 is caused to react in the presence of pyridine with an organic sulfonyl halide typified by p-toluenesulfonyl halide, alkylenesulfonyl halide or naphthylsulfonyl halide, giving a mixture of compounds 6 and 15. Such a sulfonyl halide may suitably be used also in the embodiments to come. Compound 6 has been replaced at the 3-position with a p-toluenesulfonyl group in this embodiment and compound 15 at the 4-position. This mixture is treated with 60 to 80% acetic acid to thereby unprotect each of compounds 6 and 15 at the 5- and 6-position, leading to compounds 7 and 16 in combined form. Both compounds are isolated from each other by silica gel chromatography or any other suitable technique.

Compound 7 is again masked at the 5- and 6-position with an isopropylidene group in FIG. 1 and extracted as with ethyl acetate, followed by acetylation of the 4-position hydroxyl group with acetic acid in pyridine. Compound 8 thus obtained is reacted with an aziding agent selected for example from sodium azide, potassium azide, ammonium azide or barium azide and simultaneously with 2-methoxyethanol. This reaction gives rise to a mixture of isomeric compounds 9 and 13 having at the 3-position an azido group substituted for the O-p-toluenesulfonyl group and at the 1- and 4-position two hydroxyl groups regenerated. The mixture is silica gel-chromatographed to isolate compounds 9 and 13 from each other. To selectively form compound 9, compound 8 may be reacted, prior to addition of the aziding agent, with sodium methoxide and then neutralized with acetic acid and sodium hydrogencarbonate. Particularly preferred among the above aziding agents is sodium azide for its easy handling.

By reaction with acetic anhydride in pyridine, compound 9 is acetylated at the 1- and 4-position hydroxyl groups into compound 10. This latter compound is reacted with acetic anhydride in a hydrogen atmosphere so as to cause the azido group to reduce and acetylate into an acetylamino group, leading to compound 11. A nickel based catalyst may usually be used at such stage of reaction.

Compound 11 gets unprotected upon treatment with 60 to 80% acetic acid and instead has two hydroxyl groups at the 5- and 6-position. Subsequent reaction with acetic anhydride in the presence of pyridine permits acetylation of these hydroxyl groups, thus providing compound 12, i.e. 1L-3-acetamido-1,4,5,6-tetra-O-acetyl-3-deoxy-2-O-methyl-chiro-inositol (Compound A).

Compound 1 is likewise treated to form compound 16 via compounds 5 and 15. A protective group, an isopropylidene group in FIG. 1, is introduced into compound 16 at the 5- and 6-position after which, by reaction with acetic anhydride in pyridine, the 3-position hydroxyl group is acetylated into compound 17. When reacted with an aziding agent exemplified above and simultaneously with 2-methoxyethanol, compound 17 is turned into compound 18 in which an azido group has been bonded to the 4-position and two hydroxyl groups regenerated at the 1- and 3-position. Compound 18 is reacted with acetic anhydride in pyridine to acetylate the 1- and 3-position hydroxyl groups into compound 19. By reaction with acetic anhydride in a hydrogen atmosphere, usually with use of a nickel based catalyst, compound 19 is converted to compound 20 in which the azido group has been reduced and acetylated into an acetylamino group.

Compound 20 is unprotected on treatment with 60 to 80% acetic acid with two hydroxyl groups regenerated at the 5- and 6-position, followed by reaction with acetic anhydride in pyridine, so that those hydroxyl groups are acetylated. Thus there is provided compound 21, i.e. 1L-3-acetamido-1,2,4,6-tetra-O-acetyl-3-deoxy-5O-methyl-chiro-inositol (compound B).

Figure 2A:
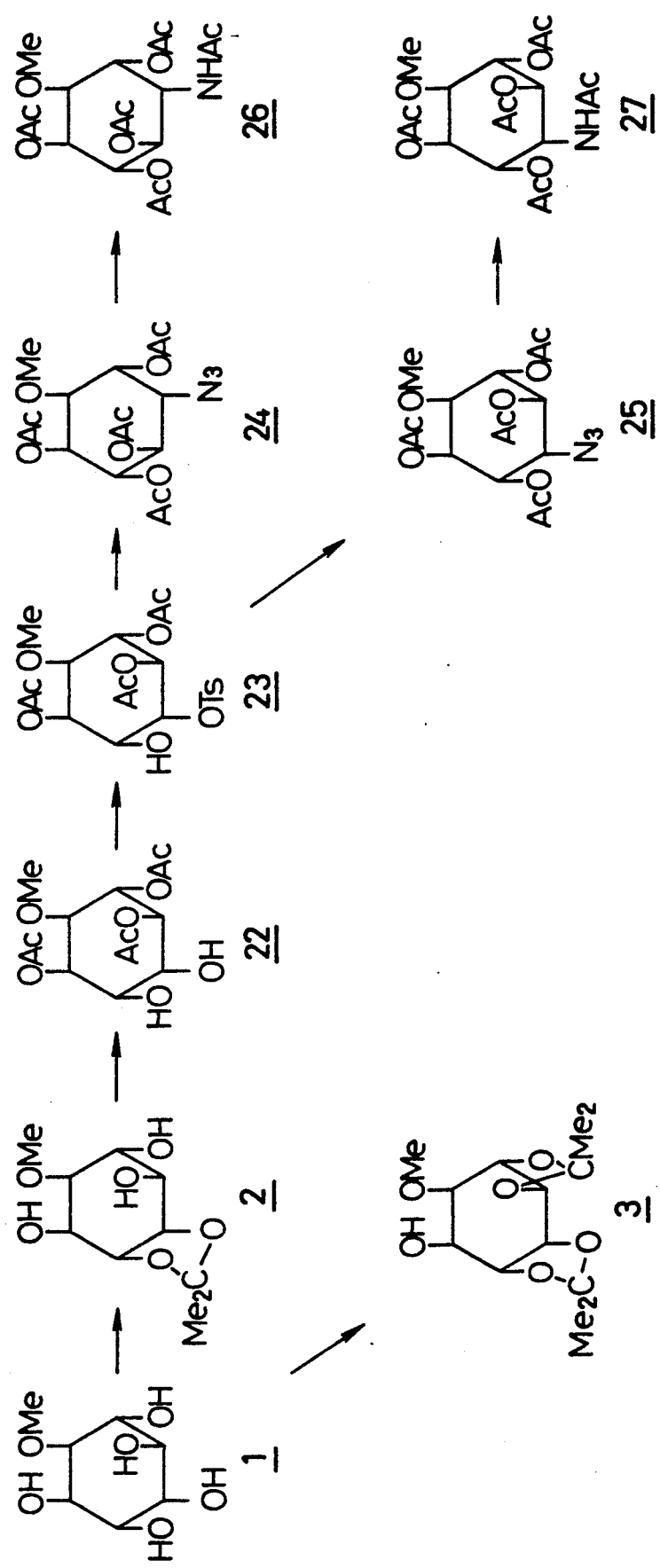
Figure 2B:
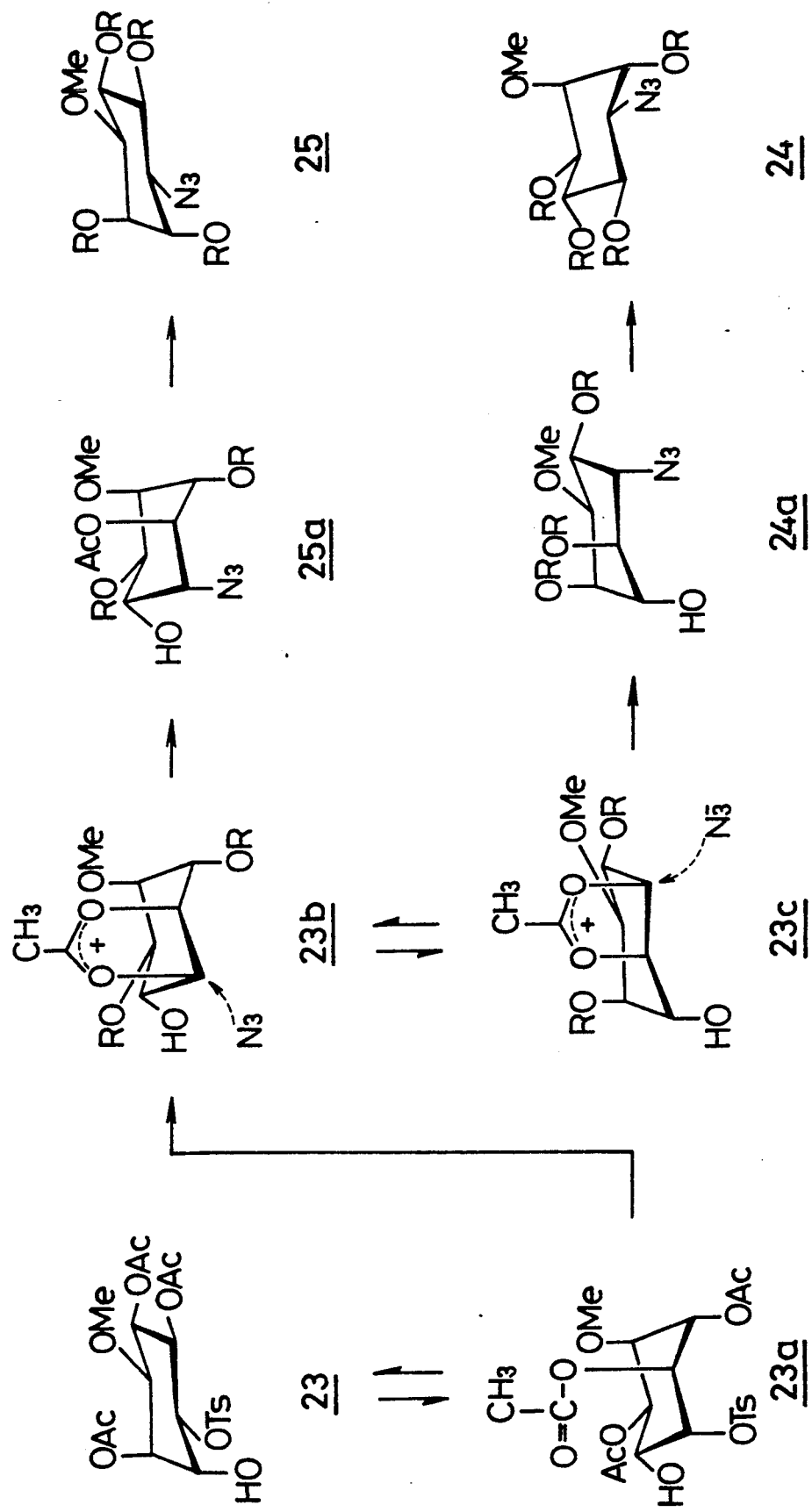

A second embodiment of the process according to the invention as shown in FIGS. 2A and 2B is directed toward the production of compounds C and D.

L-Quebrachitol 1 is treated as in the first embodiment to give a mixture of compounds 2 and 3. To the mixture are added water and ethyl acetate such that compound 2 is extracted into an aqueous phase and compound 3 into an organic phase. Compound 2 after being concentrated is reacted with acetic anhydride in the presence of pyridine, allowing the 1-, 3- and 4-position hydroxyl groups to be acetylated. Further acetic acid treatment causes the protective group to be removed and regenerates two hydroxyl groups at the 5 and 6 positions, yielding compound 22. Via a reaction with a given sulfonyl halide in pyridine, compound 22 turns into compound 23 having bonded to the 5-position oxygen atom a protective group, a p-toluenesulfonyl group in FIG. 2A.

Compound 23 is reacted with one of the above exemplified aziding agents and also with 2-methoxyethanol, whereby two tetra-O-acetyl isomers, compounds 24 and 25, are formed as an admixture. Both compounds are isolated from each other by extraction with ethyl acetate and subsequently by silica gel chromatography.

FIG. 2B is taken to refer to reaction routes from compound 23 to compounds 24 and 25, respectively. The reaction in this instance depends upon the participation of neighboring groups; namely, compound 23 is held in equilibrated relation to compound 23a which in turn is transferred to compound 23b having a cyclic acetoxonium ion attached, the last-mentioned compound being also equilibrated with compound 23c having bonded a similar cyclic ion. Each of compounds 23b and 23c at its ion-bonded portion undergoes nucleophilic substitution upon attach by an azido group and subsequent ring opening into a trans-diaxial conformation, resulting in the formation of compound 25 via compound 25a from compound 23b and of compound 24 via compound 24a from compound 23c. Compound 24 is rather convenient as compound 23c is less liable to steric hindrance at the methoxy group.

Compound 24, upon reaction with acetic anhydride in ethanol, involves the reduction and acetylation of the azio group into an acetylamino group, thus providing compound 26, i.e. 1D-2-acetamido-1,3,4,5-tetra-O-acetyl-2-deoxy-6-O-methyl-chiro-inositol (compound C).

Compound 25 is reacted as in compound 24, usually in the presence of a nickel based catalyst, and converted to compound 27, i.e. 1L-2-acetamido-1,3,4,6-tetra-O-acetyl-2-deoxy-5-O-methyl-chiro-inositol (compound D).

Figure 3:
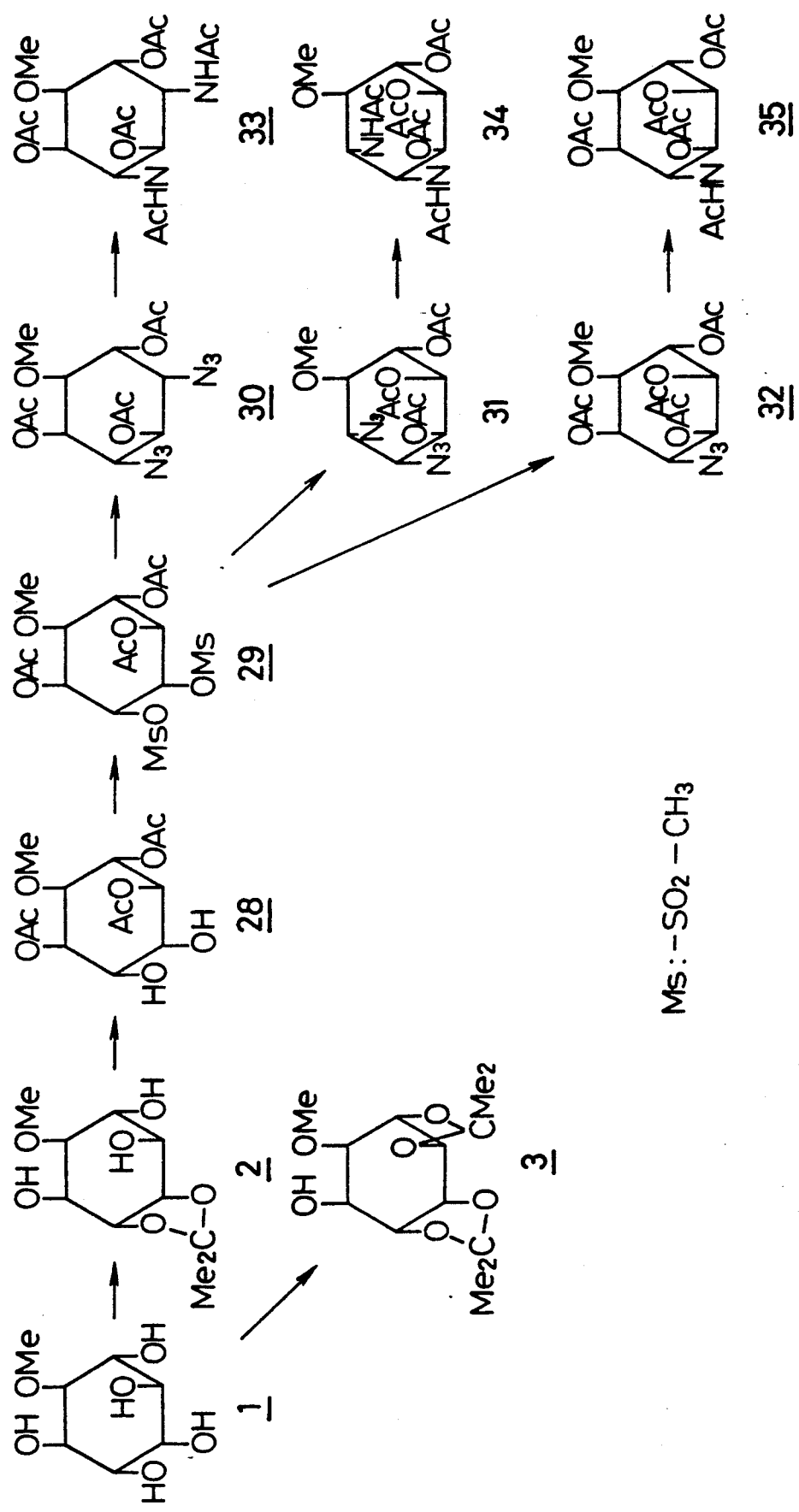

A third embodiment of the process of the invention is shown in FIG. 3 which is designed to produce compounds E to G.

Compounds 2 and 3 are derived in combined form from L-quebrachitol 1 and isolated by the procedure of the preceding embodiments. Compound 2 is reacted with acetic anhydride in pyridine to acetylate the 1-, 3- and 4-position hydroxyl groups and further treated with 60 to 80% acetic acid to unprotect the 5 and 6 positions, thereby giving compound 28. A reaction with a given sulfonyl halide in pyridine leads compound 28 to compound 29 having attached to the 5- and 6-position oxygen atoms a protective group, a methanesulfonyl group in FIG. 3.

Extracted into an organic phase is compound 29 with use of for example ethyl acetate. The thus treated compound is thereafter allowed to react with a selected aziding agent and also with 2-methoxyethanol with the results that the 4 and 6 positions, the 1 and 6 positions or the 6 position alone are replaced with azido groups. In this process stage certain substituents are inversed as viewed in FIG. 3. Positions to be azided and substituents to be inversed are made necessarily determinable, depending upon polarization of electrons in a transition state prior to compound 29 undergoing a nucleophilic reaction with an aziding agent and also upon steric hindrance of a methoxy group. Subsequent reaction of compound 29 with acetic anhydride in pyridine gives a mixture of compounds 30 to 32 each having an acetylamino group substituted for the methoxy sulfonyl group. The three compounds are isolated as by silica gel chromatography.

With addition of ethanol and usually with use of a nickel based catalyst, compound 30 is reacted with acetic anhydride to reduce and acetylate the azido group, thus providing compound 33, i.e. 1D-2,4-diacetamido-1,3,5-tri-O-acetyl-2,4-dideoxy-6-O-methyl-chiro-inositol (compound E).

Compounds 31 and 32 when reacted as in compound 30 are converted to compounds 34 and 35, respectively, i.e. 1D-1,2-diacetamido-4,5,6-tri-O-acetyl-1,2-dideoxy-3-O-methyl-chiro-inositol (compound F) and 1L-3-acetamido-1,2,4,6-tetra-O-acetyl-3-deoxy-5-O-methyl-muco-inositol (compound G).

Figure 4:
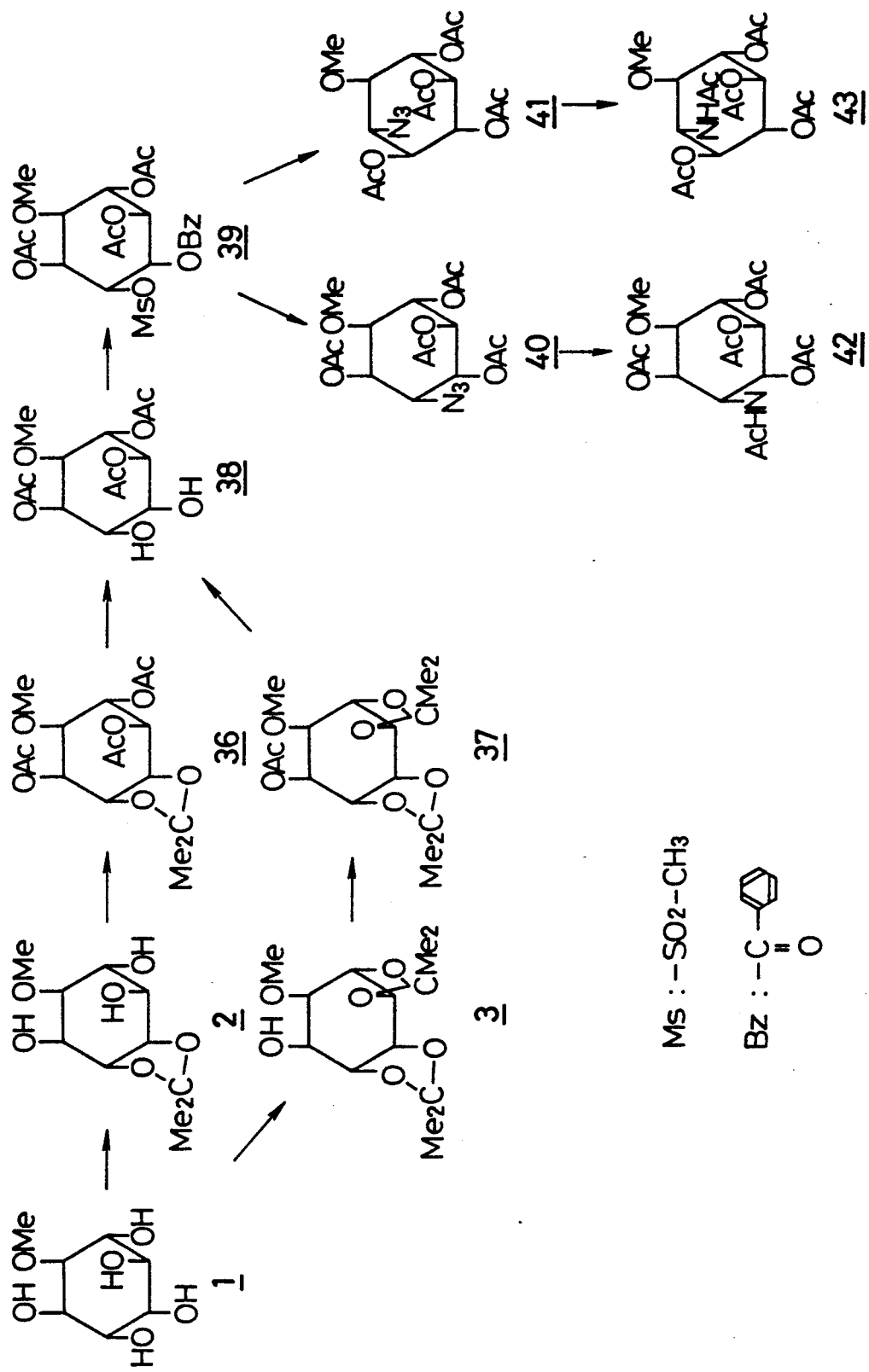

A fourth embodiment of the process of the invention as shown in FIG. 4 is directed to the production of compounds H and I.

A mixture of compounds 2 and 3 is derived from L-quebrachitol 1 and extracted as is done in the first embodiment. Compound 2 thus separated is changed, on reaction with acetic anhydride in pyridine, to compound 36 in which three hydroxyl groups have been acetylated at the 1, 3 and 4 positions. By treatment with 60 to 80% acetic acid, compound 36 gets unprotected at the 5 and 6 positions and gives compound 38. Compound 3 when reacted with acetic anhydride in pyridine is turned into compound 37 with the 1-position hydroxyl group acetylated. By the use of 60 to 80% acetic acid, compound 37 is treated to selectively unprotect the 3 and 4 positions after which, on reaction with acetic anhydride in pyridine, the 3- and 4-position hydorxyl groups are acetylated. Subsequent treatment using 60 to 80% acetic acid removes masking at the 5 and 6 positions and yields compound 38.

Compound 38 is reacted with a compound such as benzoyl chloride and then with a given sulfonyl halide so that an equatorial hydroxyl group at the 5 position and an axial counterpart at the 6 position are protected in that order. Formed via this reaction is compound 39 which is shown attached to the 5-position oxygen atom a benzoyl group and to the 6-position oxygen atom a methanesulfonyl group. On reaction with a selected aziding agent, coupled with 2-methoxyethanol, compound 39 is replaced with an azido group at the 6 position, say compound 40, and at the 1 position, say compound 41. Azidation at the 1 position results in inversion at the 1 and 6 positions. Positions to be azided and substituents to be inversed are necessarily determined due to electrons in a transition state being polarized before a nucleophilic reaction of compound 39 with an aziding agent and also to benzoyl and methanesulfonyl groups being sterically hindered.

Compounds 40 and 41 are formed as an admixture from compound 39 having been reacted with acetic anhydride in pyridine. A ratio of compound 40 to compound 41 is generally in the vicinity of 2:1. Compound 40 has one acetyl group substituted for the benzoyl group, whereas compound 41 has attached two acetyl groups in place of the benzoyl and methanesulfonyl groups.

After isolation of compounds 40 and 41 as by silica gel chromatography, each such compound is reacted with acetic anhydride in ethanol, usually in the presence of a nickel based catalyst, to thereby reduce and acetylate the azido group. Compound 40 is thus converted to compound 42, i.e. 1L-1-acetamido-2,3,4,6-tetra-O-acetyl-1-deoxy-5-O-methyl-chiro-inositol (compound H), and compound 41 to compound 43, i.e. 1D-1-acetamido-3,4,5,6-tetra-O-acetyl-1-deoxy-2-O-methyl-scyllo-inositol (compound I).

Figure 5:
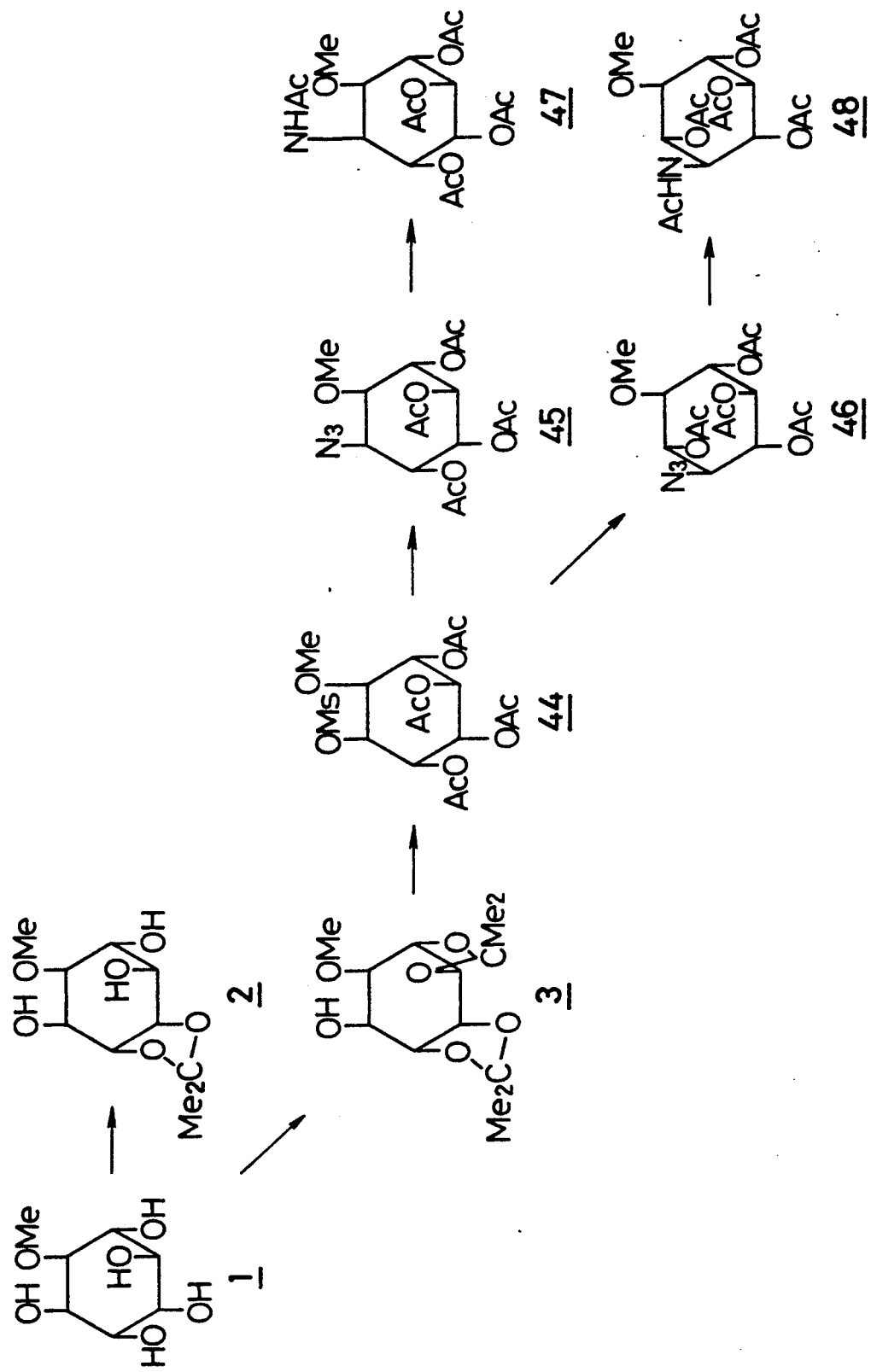

In FIG. 5 there is illustrated a fifth embodiment of the process according to the invention. Produced here are compounds J and K.

A mixture of compounds 2 and 3 is formed from L-quebrachitol 1 and then extracted to separate the two compounds as are in the preceding embodiments. After being preferably crystallized subsequent to extraction, compound 3 is reacted with a given sulfonyl halide to bond to the 1-position oxygen atom a protective group, a methanesulfonyl group in FIG. 5. Further treatment using for example hydrochloric acid unprotects both the 3 and 4 positions and the 5 and 6 positions and instead regenerates four hydroxyl groups thereat. Compound 3 thus treated is converted, by reaction with acetic anhydride in pyridine, into compound 44 in which the hydroxyl groups have been acetylated at the 3 to 6 positions.

By reaction with a selected aziding agent and also with 2-methoxyethanol, compound 44 yields a mixture of compound 45 having its 1 position azided and compound 46 having its 6 position azided. Azidation at the 6 position causes the 1 and 6 positions to be inversed as better seen from the structure of compound 46. Azidation positions and substitution inversions are rendered dependent upon polarization of electrons and steric hindrance of a methanesulfonyl group before compound 44 is nucleophilically reacted with an aziding agent.

More specifically, compound 44 is transferred, by reaction with acetic anhydride in pyridine, to compound 46 having an azido group bonded to the 6 position and an acetyl group substituted at the 1 position for the methanesulfonyl group. Compound 46 is, at this stage of reaction, in combination with compound 45. The resultant mixture is usually silica gel-chromatographed to isolate both compounds. Alternatively, the compound 45-compound 46 combination may be isolated immediately after its formation, followed by acetylation of the methanesulfonyl group located at the 1 position of compound 46.

Compound 45 is reduced in the presence of acetic anhydride and commonly also of a nickel based catalyst to thereby acetylate the azido group, thus providing compound 47, i.e. 1L-1-acetamido-3,4,5,6-tetra-O-acetyl-1-deoxy-2-O-methyl-chiro-inositol (compound J). Reduction reaction under similar conditions converts compound 46 to compound 48, i.e. 1L-1-acetamido-2,4,5,6-tetra-O-acetyl-1-deoxy-3-O-methyl-scyllo-inositol (compound K).

FIGS. 6A to 6E are taken to represent a sixth embodiment of the process according to the invention. Compounds L to O are intended to be produced.

Figure 6A:
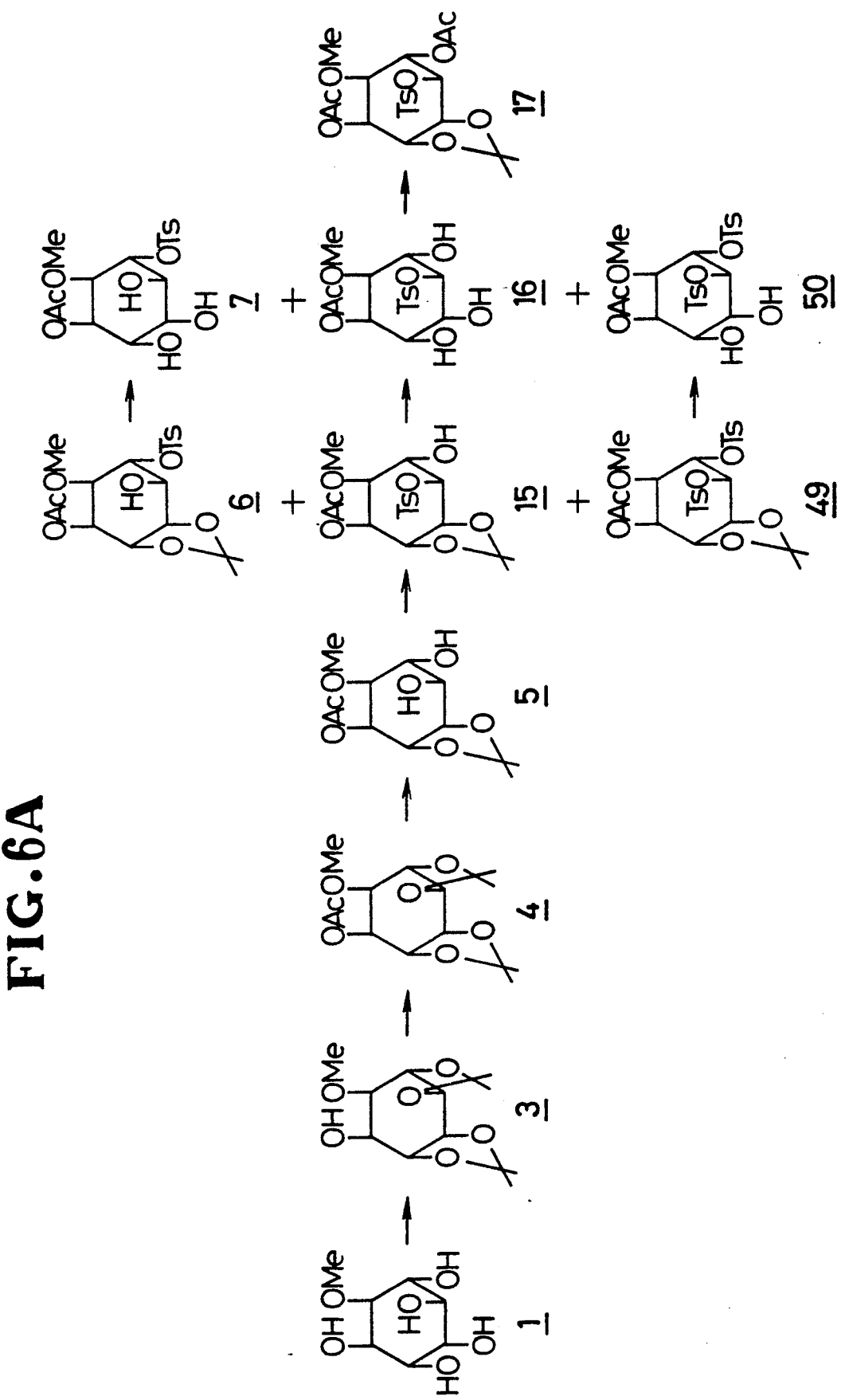
Figure 6B:
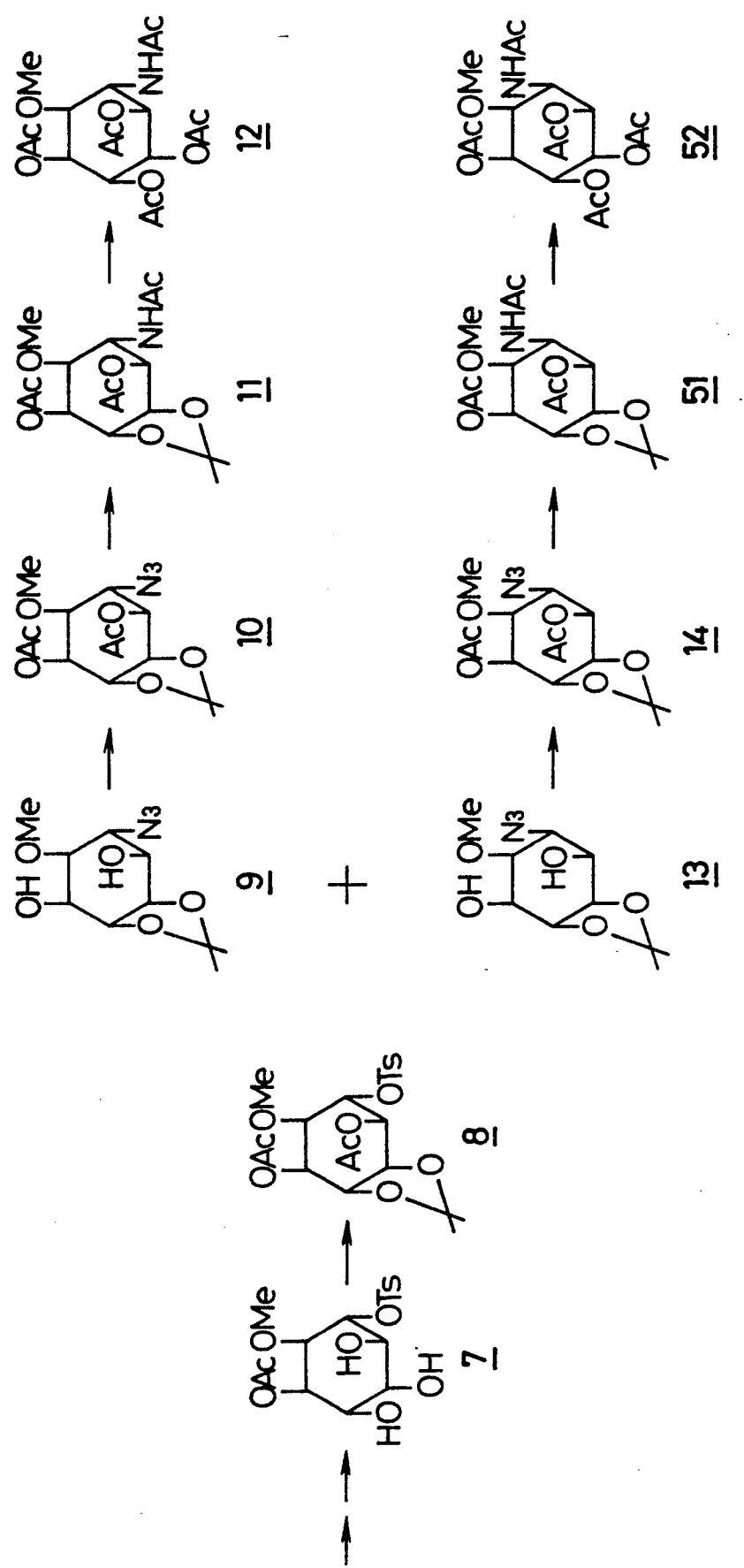
Figure 6C:
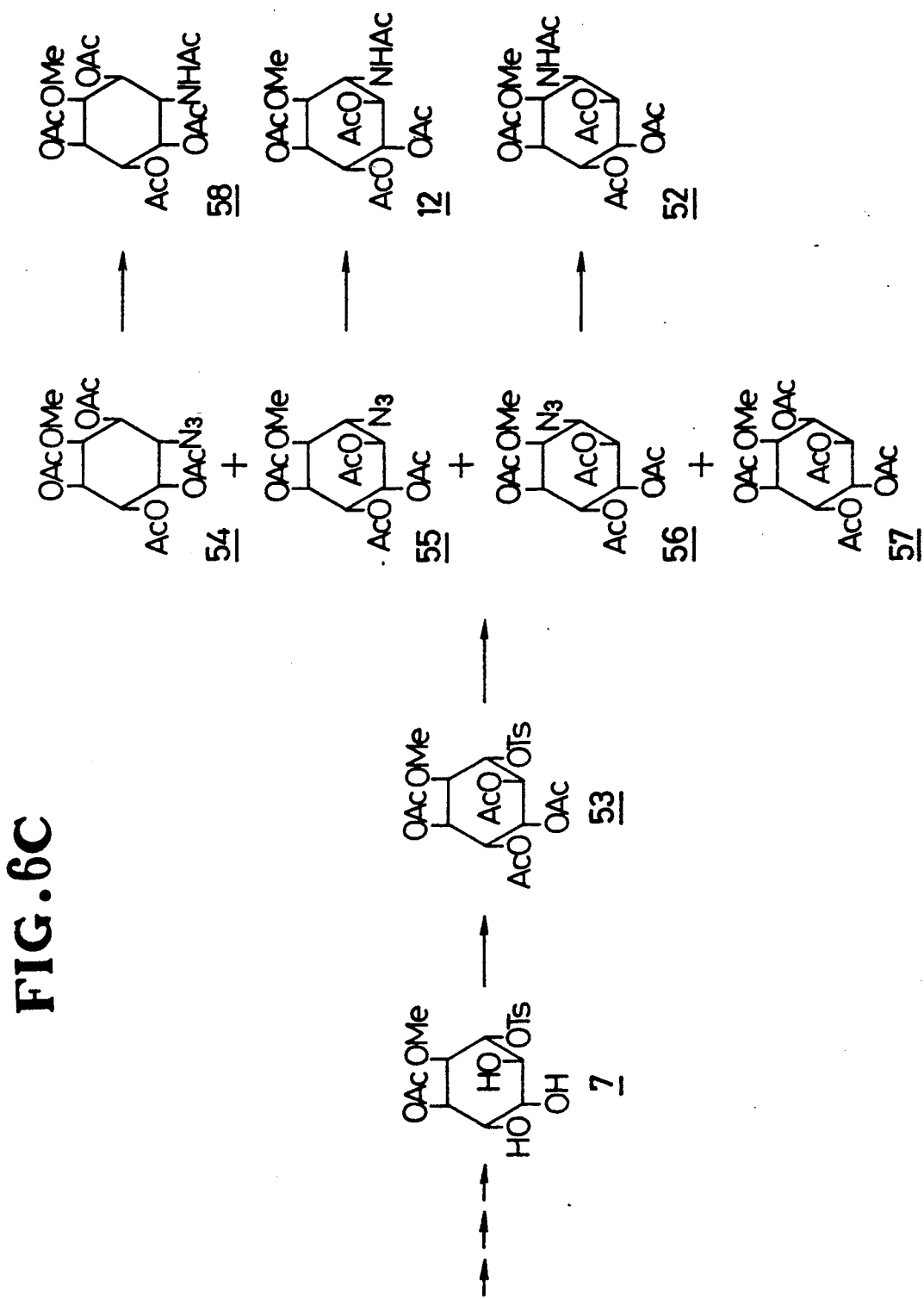
Figure 6D:
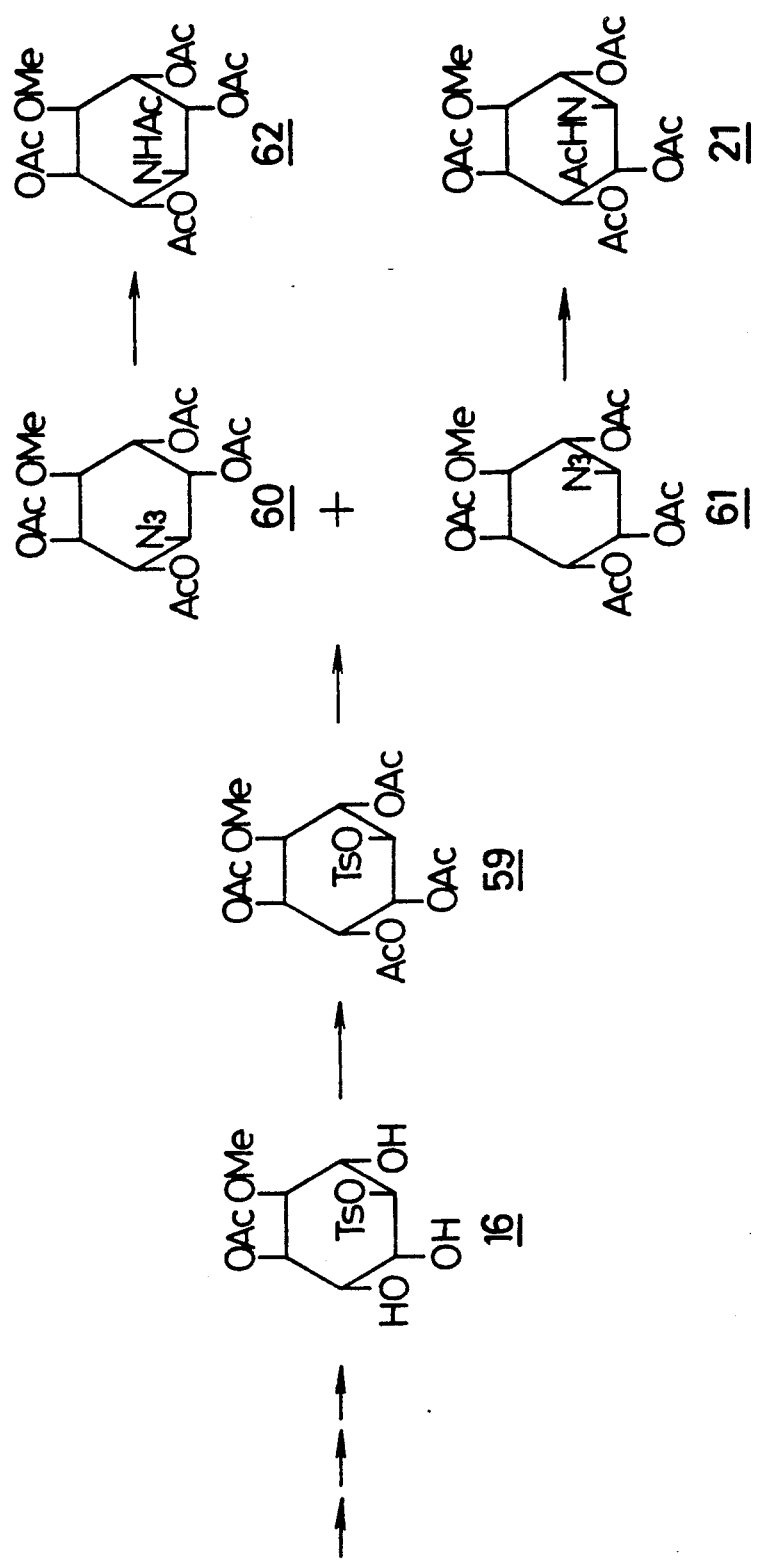

L-Quebrachitol 1 is treated with a protective precursor, 2,2-dimethoxypropane in FIG. 6A, and preferably with tosyl acid in a catalytically effective amount, thereby obtaining a mixture of compound 3 in which at both the 3 and 4 positions and the 5 and 6 positions two paired hydroxyl groups have been protected with a bridge type protective group, an isopropylidene group in FIG. 6A, and another compound (not shown) in which at the 5 and 6 positions one paired hydroxyl group has been masked with a similar protective group. With addition of ethyl acetate or like solvent to that mixture, compound 3 is extracted into an organic phase. The protective group is used generally in a proportion of about 5 equivalents, but greater proportions up to about 10 equivalents will lead to higher yields of compound 3.

Compound 3 when reacted with acetic anhydride in pyridine is converted to compound 4 with the sole hydroxyl group at the 1 position of compound 3 being acetylated. Compound 4 is highly crystalline in nature. By treatment with 60 to 80% acetic acid and by subsequent stirring at room temperature and concentration in vacuo, compound 4 is allowed to selectively remove the 3- and 4-position protective group, trans-isopylidene, so that compound 5 is obtained. To prevent formation of a tetraol which may occur from concurrent removal of the 5- and 6-position protective group, cis-isopropylidene, and of the 3- and 4-position counterpart, vacuum concentration should be effected preferably at about 20° C. in a bath.

On reaction with a given sulfonyl halide, a p-toluenesulfonyl group in FIG. 6A, in the presence of pyridine, compound 5 gives compounds 6, 15 and 49 in combined form. Compound 6 has the sulfonyl group at the 3 position, compound 15 at the 4 position and compound 49 at the 3 and 4 positions. When the combination compound is treated at about 60° C. with 60 to 80% acetic acid, each of compounds 6, 15 and 49 is made free from protection at the 5 and 6 positions, thereby giving a mixture of triols or compounds 7 and 16 and a diol or compound 50. The three compounds are isolated as by silica gel chromatography.

A protective group, an isopropylidene group in FIG. 6B, is again introduced to the 5- and 6-position hydroxyl groups of compound 7 which is then extracted as with a ethyl acetate. Subsequent reaction with acetic anhydride in pyridine permits acetylation of the 4-position hydroxyl group, leading to compound 8. Compound 16 is treated and reacted as in compound 7 into compound 17.

By reaction with an excessive amount of a selected aziding agent in 2-methoxyethanol, compound 8 forms a mixture of compounds 9 and 13 in a ratio of 4:1. Both compounds have an azido group substituted at the 3 position for the O-p-toluenesulfonyl group and two hydroxyl groups regenerated at the 1 and 4 positions. Compounds 9 and 13 are isolated as by silica gel chromatography.

Compound 13 is changed into compound 14 via a reaction with acetic anhydride in pyridine in which the 1- and 4-hydroxyl groups of the former compound are acetylated. Compound 14 is of an allo type due to an $S_N2$ type reaction. By reaction with acetic anhydride in a hydrogen atmosphere and usually in the presence of a nickel based catalyst, compound 14 undergoes reduction and acetylation of its azido group into an acetylamino group, thus forming compound 51. Treatment using 60 to 80% acetic acid causes compound 51 to remove the protective group and hence regenerate two hydroxyl groups at the 5 and 6 positions. Subsequent reaction with acetic anhydride in pyridine acetylates the 5- and 6-position hydroxyl groups, providing compound 52, i.e. 1D-2-acetamido-1,4,5,6-tetra-O-acetyl-2-deoxy-3-O-methylallo-inositol (compound L).

Compound 9 is reacted with acetic anhydride in pyridine to thereby acetylate the 1- and 4-position hydroxyl into compound 10. This compound has an L-chiro type resulting from the participation of neighboring groups and retaining the stereochemistry of compound 8. A similar set of reaction conditions employed to obtain compound 52 via compounds 14 and 51 may be followed in converting compound 10 to compound 11 from which compound A is derived.

Compound 1 is likewise treated to form compound 7 via compound 5. By reaction with acetic anhydride in pyridine, compound 7 causes acetylation of the 4-, 5- and 6-position hydroxyl groups and turns into compound 53 in FIG. 6C. When compound 53 is acetylated with an excessive amount of a selected aziding agent in 2-methoxyethanol and further with acetic anhydride in pyridine, there is obtained a combination of three azided structures, compounds 54, 55 and 56, and one pentaacetylated structure, compound 57, in a ratio of about 7:7:1:4. Compounds 54 to 56 are isolated as by silica gel chromatography.

Compound 54 undergoes, on reaction with acetic anhydride in a hydrogen atmosphere, reduction and acetylation of the azido group into an acetylamino group, providing compound 58, i.e. 1D-1-acetamido-2,3,4,6-tetra-O-acetyl-1-deoxy-5-O-methyl-neo-inositol (compound M).

Compounds 55 and 56 may be treated as is in compound 54 into compounds A and L, respectively.

Compound 1 is likewise treated to derive compound 16 from compound 5. As viewed in FIG. 6D, the 3-, 5- and 6-position hydroxyl groups of compound 16 are acetylated by reaction with acetic anhydride in pyridine, whereby compound 59 is prepared. Under the same reaction conditions as in compound 53, compound 59 turns into two azided structures, compounds 60 and 61, in combined form. In this reaction stage an acetoxonium ring is formed, owing to the participation of neighboring groups, at the 3 and 4 positions or at the 4 and 5 positions. Experiments have revealed that such participation takes place predominantly at the 4 and 5 positions, meaning that compound 59 yields a major proportion of compound 60 having a methoxy group equatorially attached. Compounds 60 and 61 are isolated by silica gel chromatography.

By reaction with acetic anhydride in a hydrogen atmosphere, compound 60 is caused to reduce and acetylate the azido group into an acetylamino group, thereby providing compound 62, i.e. 1D-3-acetamido-1,2,4,5-tetra-O-acetyl-3-deoxy-6-O-methyl-chiro-inositol (compound N). Compound 61 may be likewise reacted into compound B.

Figure 6E:
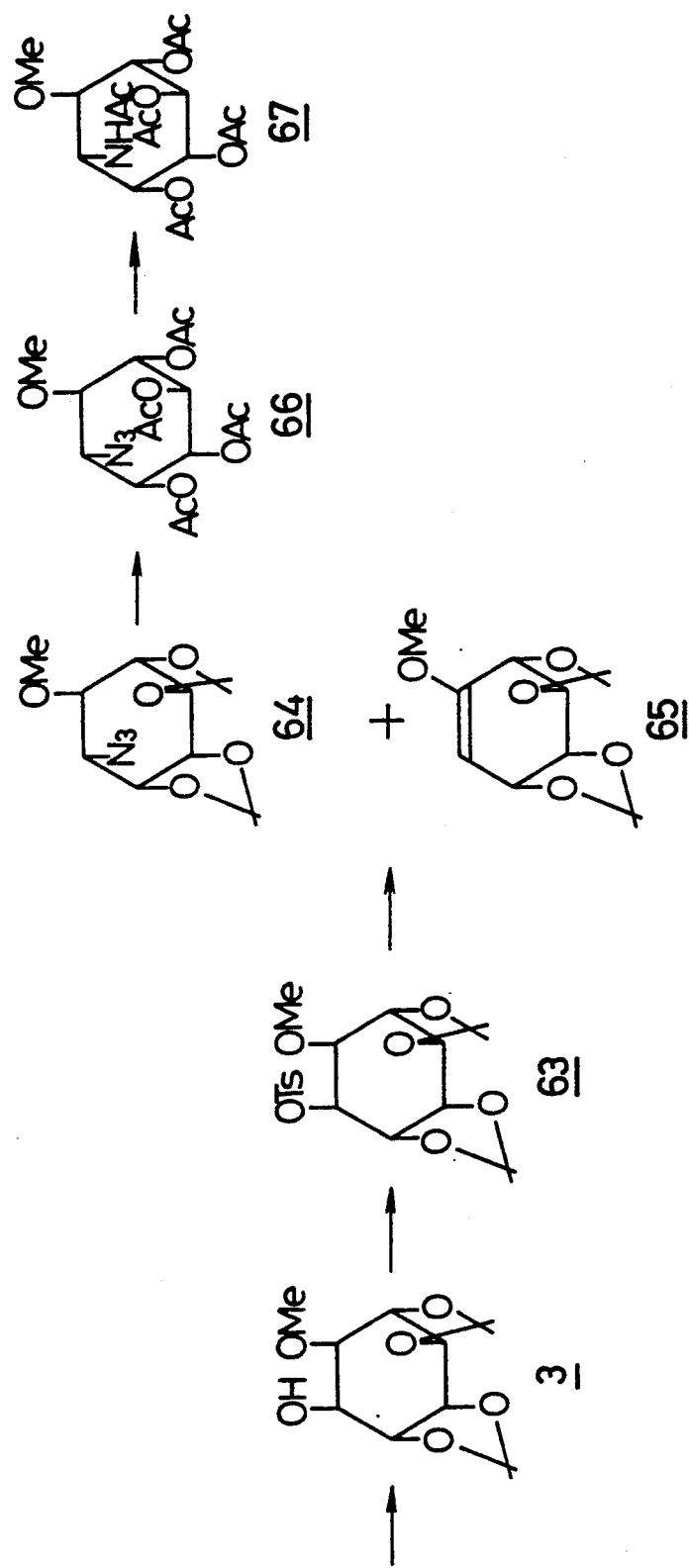

In FIG. 6E compound 3 prepared from compound 1 is reacted with a given sulfonyl halide in pyridine so that compound 63 is obtained as shown bonded a p-toluenesulfonyl group to the 1 position. Upon reaction with an excessive amount of a selected aziding agent in the presence of dimethyl sulfoxide, compound 63 gives a combination of compounds 64 and 65 in a ratio of about 4:1. Compound 64 has an azide structure resulting from an $S_N2$ type reaction and compound 65 a cyclohexene structure from an elimination reaction. As by silica gel chromatography the two compounds are isolated from each other.

Compound 64 is reacted with about 1 to 4M hydrochloric acid to remove the protective group and hence regenerate four hydroxyl groups at the 3 to 6 positions. Subsequent reaction with acetic anhydride in pyridine permits acetylation of these hydroxyl groups, leading to compound 66 of a tetraacetyl structure. When compound 66 is reacted with acetic anhydride in a hydrogen atmosphere, the azido group is reduced and acetylated into an acetylamino group. Thus compound 67 is provided which is contemplated under the invention as 1L-1-acetamido-2,3,4,5-tetra-O-acetyl-1-deoxy-6-O-methyl-myo-inositol (compound O).

Extraction, concentration, desalting, purification and other necessary treatments may be carried out, where desired, at the reaction stages in the process according to the invention.

The following examples are given to further illustrate the invention. These examples should be regarded as illustrative rather than restrictive.

EXAMPLE 1

1L-1,4-di-O-acetyl-3-azido-3-deoxy-5,6-O-isopropylidene-2-O-methyl-chiro-inositol (compound 10) and 1D-1,4-di-O-acetyl-2-azido-2-deoxy-5,6-O-isopropylidene-3-O-methyl-allo-inositol (compound 14)

a) To L-quebrachitol 1 (10.0 g, 51.5 mmol) were dimethylformamide (DMF)(100 ml), 2,2-dimethoxypropane (31 ml, 250 mmol) and p-toluenesulfonyl chloride (0.5 g). The whole was about 4 in pH. Stirring was done at room temperature for 16 hours. The reaction mixture was neutralized with sodium hydrogencarbonate and thereafter incorporated with ethyl acetate (300 ml) and water (300 ml). Extracted by shaking were into an aqueous phase 1L-5,6-O-isopropylidene-2-O-methyl-chiro-inositol (compound 2) and into an organic phase 1L-1,2:3,4-di-O-isopropylidene-5-methyl-chiro-inositol (compound 3).

After drying with sodium sulfate anhydride, the resulting organic phase was filtered to remove sodium sulfate. In vacuo concentration of the filtrate gave a pale yellowish syrup (6.9 g). To the syrup were added pyridine (50 ml) and acetic anhydride (50 ml), and reaction was made with stirring at room temperature for 26 hours. With addition of toluene the reaction mixture was azeotropically concentrated in vacuum. There was obtained a brown crude crystal (7.54 g) which was then recrystallized from ethanol to prepare 1L-1-O-acetyl-3,4:5,6-di-O-isopropylidene-2-O-methyl-chiro-inositol (compound 4) (5.39 g, 33% yield).

compound 4

Rf: 0.72 (MEK/toluene=2/1, v/v).
mp: 109°–109.5° C. (ethanol).
IR (neat): 1750 cm$^{-1}$ (OAc).
$^1$H-NMR (δ, 90 MHz, CDCl$_3$): 5.55 –5.43 (m, 1H, H-6), 4.40–4.20 (m, 2H, H-1, 2), 3.80–3.50 (m, 3H, H-3, 4, 5), 3.43 (s, 3H, OMe), 2.14 (s, 3H, OAc), 2.50, 1.45, 1.36 (3s, 3H, 6H, 3H, 2×CMe$_2$).
elementary analysis as C$_{15}$H$_{24}$O$_7$ (%): C: 56.95, H: 7.65 (calculated). C: 57.00, H: 7.48 (found).
$[\alpha]_D^{25}$: +2.1° (c, 1.03, CHCl$_3$)

b) Compound 4 (12.71 g, 40.18 mmol) was mixed with 80% acetic acid and stirred at room temperature for 4 hours. The reaction mixture on addition of toluene was subjected to azeotropic concentration in vacuo. 1L-1-O-Acetyl-5,6-O-isopropylidene-2-O-methyl-chiro-inositol (compound 5) was obtained as a syrup (12.2 g) which was subsequently incorporated with p-toluenesulfonyl chloride (11.49 g, 60.27 mmol) and pyridine (80 ml), followed by stirring at room temperature for 20 hours. The reaction liquid after being diluted with ethyl acetate (300 ml) was washed three times with water (each 100 ml). Upon drying of the resulting organic phase with sodium sulfate anhydride, filtration is done to remove the drying agent used. The filtrate was azeotropically concentrated in vacuo and with toluene, whereby a pale yellow syrup (18.5 g) was obtained as a combination of 1L-1-O-acetyl-5,6-O-isopropylidene-2-O-methyl-3-O-(p-toluenesulfonyl)-chiro-inositol (compound 6) and 1L-1-O-acetyl-5,6-O-isopropylidene-2-O-methyl-4-O-(p-toluenesulfonyl)-chiro-inositol (compound 15).

The above combination compound was incroporated with 80% acetic acid (80 ml), followed by stirring in an oil bath at 50° C. for 16 hours. By toluene-azeotropy the reaction mixture was vacuum-condensed into a syrup-like residue (18.8 g). Purification by silica gel chromatography (ethyl acetate/toluene=3/2 - 1/0) gave as a foamy syrup 1L-1-O-acetyl-2-O-methyl-3-O-(p-toluenesulfonyl)-chiroinositol (compound 7) (4.79 g, 31% yield based on compound 4) and as a white solid 1L-1-O-acetyl-2-O-methyl-4-O-(p-toluenesulfonyl)-chiro-inositol (compound 16) (3.36 g, 21% yield based on compound 4).

compound 7

Rf: 0.29 (MEK/toluene=1/1, v/v).
mp: syrup.
elementary analysis as $C_{16}H_{22}O_9S \cdot \frac{1}{2}H_2O$ (%): C: 48.11, H: 5.80 (calculated). C: 48.12, H: 5.66 (found).
$[\alpha]_D^{23}$: $-39.4°$ (c, 2.86, $CH_3OH$)

compound 16

Rf: 0.54 (MEK/toluene=1/1, v/v).
mp: 162°-163° C. (ethanol).
elementary analysis as $C_{16}H_{22}O_9S$ (%): C: 49.22, H: 5.68 (calculated). C: 49.00, H: 5.66 (found).
$[\alpha]_D^{23}$: $-23.4°$ (c, 1.185, $CH_3OH$)

c) To compound 7 (4.71 g, 12.06 mmol) were added DMF (50 ml), p-toluenesulfonate monohydrate (200 mg) and 2,2-dimethoxypropane (7.41 mg, 60.3 mmol), and stirring was conducted at 55° C. for 23 hours. The reaction mixture was neutralized with sodium hydrogencarbonate, followed by addition of ethyl acetate (300 ml) and by subsequent washing with water (3 times each 100 ml). The resulting organic phase was dried with sodium sulfate anhydride and filtered to remove the drying agent. In vacuo concentration of the filtrate by azeotropy with toluene led to a brown syrup (5.8 g).

Reaction of that syrup was made with addition of pyridine (30 ml) and acetic anhydride (20 ml) and at room temperature for 19 hours. While in toluene-azeotropy the reaction mixture was vacuum-concentrated to obtain a brown syrup (6.50 g). Silica gel-chromatographing (MEK/toluene=1/6) gave as a colorless syrup 1L-1,4-di-O-acetyl-5,6-O-isopropylidene-2-O-methyl-3-O-(p-toluenesulfonyl)-chiro-inositol (compound 8) (3.66 g, 64% yield).

compound 8

Rf: 0.49 (MEK/toluene=1/5, v/v).
IR (neat) : 1755 cm$^{-1}$ (OAc). 1180 cm$^{-1}$ ($SO_2$).
$^1$H-NMR ($\delta$, 90 MHz, $CDCl_3$): 7.80 -7.30 (2d, each 2H, J=9.0 Hz, $SO_2$ PhMe), 5.59 (t, 1H, $J_{1,2}=J_{1,6}=3.0$ H$^z$, H-1), 5.37 -5.11 (m, 1H, H-4), 4.81 (dd, 1H, $J_{2,3}=7.8$ Hz, $J_{3,4}=9.5$ Hz, H-3), 4.36 -4.14 (m, 2H, H-5, 6), 3.61 (dd, 1H, H-2), 3.19 (s, 3H, OMe), 2.44 (s, 3H, PhMe), 2.14, 2.04 (2s, each 3H, 2×OAc), 1.53, 1.34 (2s, each 3H, $CMe_2$).
mp: syrup.
elementary analysis as $C_{21}H_{28}O_{10}S$ (%): C: 53.33, H: 5.97 (calculated). C: 53.01, H: 6.04 (found).
$[\alpha]_D^{18}$: $-65.6°$ (c, 0.94, $CHCl_3$).

d) Compound 8 (875 mg, 1.83 mmol) was incorporated with sodium azide (476 mg, 7.32 mmol) and aqueous 90% 2-methoxyethanol (10 ml). Refluxing was done in an oil bath at 125° C. for 20 hours. After being azeotropically vacuum-concentrated with toluene, the reaction liquid was diluted with ethyl acetate and filtered to remove deposited salts. A pale yellow syrup (0.46 mg) was derived from in vacuo concentration of the filtrate and thereafter purified by silica gel chromatography (ethanol/toluene=1/17) to obtain as a white solid 1L-3-azido-3-deoxy-5,6-O-isopropylidene-2-O-methyl-chiro-inositol (compound 9) (272 mg, 57% yield) and as a colorless syrup 1D-2-azido-2-deoxy-5,6O-isopropylidene-3-O-methyl-allo-inositol (compound 13) (66 mg, 14% yield). Compound 9 was recrystallized from ethanol for analysis.

Compound 9

Rf: 0.37 (ethanol/toluene=$\frac{1}{8}$, v/v).
mp: 80°-81° C. (ethanol).
elementary analysis as $C_{10}H_{17}N_3O_5$ (%): C: 46.33, H: 6.61, N: 15.92 (calculated). C: 46.47, H: 6.38, N: 16.21 (found).
$[\alpha]_D^{21}$: $-34.7°$ (c, 0.2, $CHCl_3$).

compound 13

Rf: 0.41 (ethanol/toluene=$\frac{1}{8}$, v/v).
mp: syrup.
elementary analysis as $C_{10}H_{17}N_3O_5$ (%): C: 46.33, H: 6.61, N: 16.21 (calculated). C: 46.11, H: 6.39, N: 16.41 (found).
$[\alpha]_D^{24}$: $-28.3°$ (c, 0.96, $CHCl_3$).

e) To compound 9 (15 mg, 58 μmol) were added pyridine (1 ml) and acetic anhydride (1 ml), and stirring was conducted at room temperature for 6 hours. From toluene-azeotropy, vacuum-concentration of the reaction mixture, a brown syrup (21 mg) was derived which was then silica gel-chromatographed (ethyl acetate/hexane=1/6) to give as a white crystal title compound 10 (19 mg, 97% yield). Subsequent recrystallization was made from ethanol.

compound 10

Rf: 0.39 (ethyl acetate/hexane=$\frac{1}{8}$, v/v).
mp: 123.5°-124.5° C. (ethanol).
IR (neat): 2110 cm$^{-1}$ ($N_3$). 1750 cm$^{-1}$ (OAc).
$^1$H-NMR ($\delta$, 90 MHz, $CDCl_3$): 5.70 (t, 1H, $J_{1,2}=J_{1,6}=2.7$ Hz, H-1), 5.16-4.85 (m, 1H, H-4), 4.28-4.05 (m, 2H, H-5, 6), 3.68 (t, 1H, $J_{2,3}=J_{3,4}=10.0$ Hz, H-3), 3.48 (dd, 1H, H-2), 3.46 (s, 3H, OMe), 2.15, 2.14 (2s, each 3H, 2×OAc), 1.54, 1.34 (2s, each 3H, $CMe_2$),
elementary analysis as $C_{14}H_{21}N_3O_7$ (%): C: 48.98, H: 6.17, N: 12.24 (calculated). C: 48.82, H: 6.03, N: 11.87 (found).
$[\alpha]_D^{24}$: $-94.9°$ (c, 0.65, $CHCl_3$).

f) Compound 13 (18 mg, 69 μmol) after being incorporated with pyridine (1 ml) and acetic anhydride (1 ml) was reacted with stirring at room temperature for 6 hours. A brown syrup (23 mg) was formed by toluene-azeotropy, vacuum-concentration of the reaction mixture. The syrup product was silica gel-chromatographed (ethyl acetate/hexane=1/6) after which title compound 14 was obtained as a white crystal. The resulting compound was further recrystallized from ethanol.

compound 14

Rf: 0.39 (ethyl acetate/hexane=$\frac{1}{8}$, v/v).
mp: 85°-86° C. (ethanol).
IR (neat): 2110 cm$^{-1}$ ($N_3$). 1750 cm$^{-1}$ (OAc).
$^1$H-NMR ($\delta$, 90, MHz, $CDCl_3$): 5.61 (ddd, 1H, $J_{1,2}=3.0$ Hz, $J_{1,3}=1.0$ Hz, $J_{1,6}=4.0$ Hz, H-1). 4.95 (dd, 1H, $J_{3,4}=3.0$ Hz, $J_{4,5}=7.0$ Hz, H-4) 4.42 -4.19 (m, 2H, H-5, 6). 4.15 (ddd, 1H, $J_{1,3}=1.0$ Hz, $J_{2,3}=4.0$ Hz, $J_{3,4}=3.0$ Hz, H-3). 3.77 (dd, 1H, $J_{1,2}=3.0$ Hz, $J_{2,3}=4.0$ Hz, H-2). 3.46 (s, 3H, OMe). 2.19, 2.17 (2s, each 3H, 2×OAc). 1.56, 1.44 (2s, each 3H, $CMe_2$).

elementary analysis as $C_{14}H_{21}N_3O_7$ (%): C: 48.98, H: 6.17, N : 12.24 (calculated). C: 49.14, H: 6.06, N : 12.09 (found).

$[\alpha]_D^{24}$: 89.1° (c, 0.65, $CHCl_3$).

EXAMPLE 2

1L-3-acetamido-1,4,5,6-tetra-O-acetyl-3-deoxy-2-O-methyl-chiro-inositol (compound 12) (compound A)

a) To compound 8 (2.53 g, 5.36 mmol) provided in Example 1 was added 1M dodium methoxide (10 ml), and stirring was effected at 0° C. for 15 minutes and then at room temperature for 24 hours. The reaction mixture was neutralized with sodium hydrogencarbonate and concentrated in vacuo. The concentrate on addition of ethyl acetate was filtered to remove salts deposited.

In vacuo concentration converted the resultant filtrate to a pale yellow syrup (1.1 g). To the syrup wre incorporated sodium azide (1.39 g, 21.4 mmol), ammonium chloride (1.14 g, 21.4 mmol) and aqueous 90% 2-methoxyethanol (10 ml), and refluxing was performed in an oil bath at 120° C. for one hour. The reaction liquid was treated with addition of ethyl acetate and filtered to remove deposited salts. On toluene-azeotropy, vacuum-concentration of the filtrate, compound 9 (1.5 g) was obtained as a brown syrup. Compound 9 after being mixed with pyridine (6 ml) and acetic anhydride (6 ml) was stirred at room temperature for 6 hours. Subsequent vacuum concentration by azeotropy with toluene gave a brown syrup (2.0 g) which was then silica gel-chromatographed (ethyl acetate/hexane=1/6), thereby obtaining as a white solid compound 10 (1.52 g, 83% yeild based on compound 8).

b) To compound 10 (1.52 g, 4.44 mmol) were added ethanol (15 ml), acetic anhydride (2.1 ml) and Raney nickel-T4 catalyst (an amount of 2 small spatulas). Stirring was conducted in a hydrogen atmosphere at one atm for 22 hours. After removal of the catalyst by filtration, the filtrate was subjected to toluene-azeotropy, vacuum-concentration, whereby a green syrup (2.3 g) was formed. Silica gel-chromatographing (ethanol/toluene=1/12) gave as a white crystal 1L-3-acetamido-1,4-di-O-acetyl-3-O-deoxy-5,6-O-isopropylidene-2-O-methyl-chiro-inositol (compound 11) (1.58 g, 99% yield). The resulting compound was further recrystallized from ethanol.

compound 11

Rf: 0.31 (ethanol/toluene=1/10, v/v).
mp: 128°-129° C. (ethanol).
IR (neat) : 3300 $cm^{-1}$ (NH), 1745 $cm^{-1}$ (OAc), 1660 $cm^{-1}$ (amide), 1550 $cm^{-1}$ (amide),
$^1$H-NMR ($\delta$, 90 MHz, $CDCl_3$): 9.43 (d, 1H, $J_{3,NH}$=8.0 Hz, NH), 5.37 (dd, 1H, $J_{1,2}$=3.0 Hz, $J_{1,6}$=5.0 Hz, H-1), 4.99 (dd, 1H, $J_{3,4}$=10.0 Hz, $J_{4,5}$=9.0 Hz, H-4), 4.50–4.30 (m, 2H, H-5, 6), 4.16 (ddd, 1H, $J_{2,3}$=5.0 Hz, H-3), 3.52 (dd, 1H, $J_{1,2}$=3.0 Hz, H-2), 3.46 (s, 3H, OMe), 2.15, 2.11, 1.96 (3s, each 3H, NHAc, 2×OAc), 1.48, 1.35 (2s, each 3H, $CMe_2$),
elementary analysis as $C_{16}H_{25}NO_8$ (%): C: 53.47, H: 7.01, N : 3.90 (calculated). C: 53.12, H: 6.85, N : 3.61 (found).
$[\alpha]_D^{23}$: $-37.4°$ (c, 1.17, $CHCl_3$).

c) Compound 11 (40 mg, 0.11 mmol) was mixed with 75% acetic acid (1 ml) and stirred at 55° C. for 15 hours. A white solid (38 mg) was obtained by toluene-azeotropy, vacuum-concentration of the reaction mixture. To the solid product were added pyridine (1 ml) and acetic anhydride (1 ml), and stirring was done at room temperature for 18 hours. The resulting reaction liquid was vacuum-concentrated by toluene-azeotropy to give a white solid (46 mg). Purification by silica gel chromatography (ethanol/toluene=$\frac{1}{5}$) provided as a white solid title compound 12 or ultimate compound A (39 mg, 89% yield). The resulting compound was further recrystallized from ethanol.

compound 12 (compound A)

Rf: 0.50 (ethanol/toluene=1/5, v/v).
mp: 187°-188° C. (ethanol).
IR (neat): 3350 $cm^{-1}$ (NH), 1750 $cm^{-1}$ (OAc), 1730 $cm^{-1}$ (OAc), 1650 $cm^{-1}$ (amide), 1550 $cm^{-1}$ (amide).
$^1$H-NMR ($\delta$, 90 MHz, $CDCl_3$): 5.60 –5.20 (m, 5H, H-1, 4, 5, 6, NH), 4.50 –4.15 (m, 1H, H-3), 3.55 (dd, 1H, $J_{1,2}$=3.0 Hz, $J_{2,3}$=11.0 Hz, H-2), 3.35 (s, 3H, OMe), 2.19, 2.14, 2.03, 1.99, 1.98 (5s, each 3H, NHAc, 4×OAc).
elementary analysis as $C_{17}H_{25}NO_{10}$ (%): C: 50.62, H: 6.25, N : 3.47 (calculated). C: 50.53, H: 6.03, N : 3.34 (found).
$[\alpha]_D^{21}$: $-13.9°$ (c, 0.79, $CHCl_3$).

EXAMPLE 3

1L-3-acetamido-1,2,4,6-tetra-O-acetyl-3-deoxy-5-O-methyl-chiro-inositol (compound 21) (compound B)

a) To compound 16 (401 mg, 1.03 mmol) were added DMF (4 ml), p-toluenesulfonate monohydrate (25 mg) and 2,2-dimethoxypropane (0.63 ml, 5.14 mmol). Stirring was done at 55° C. for 20 hours. After neutralization with sodium hydrogencarbonate and treatment with ethyl acetate, the reaction mixture was filtered to remove salts having been deposited. By toluene azeotropy the filtrate was concentrated in vacuuo to obtain a brown syrup (540 mg). The resultant syrup after being incorporated with pyridine (3 ml) and acetic anhydride (3 ml) was reacted with stirring at room temperature for 14 hours. Toluene-azeotropy, vacuum-concentration led the reaction liquid to a brown syrup (660 mg) which was then purified by silica gel chromatography (MEK/toluene=1/6), preparing 1L-1,3-di-O-acetyl-5,6-O-isopropylidene-2-O-methyl-4-O-(p-toluenesulfonyl)-chiro-inositol (compound 17) (438 mg, 90% yield).

compound 17

Rf: 0.49 (MEK/toluene=1/5, v/v).
IR (neat) : 1755 $cm^{-1}$ (OAc), 1180 $cm^{-1}$ ($SO_2$).
$^1$H-NMR ($\delta$, 90 MHz, $CDCl_3$): 7.80, 7.30 (2d, each 2H, J=9.0 Hz, $SO_2PhMe$), 5.45 (dd, 1H, $J_{1,2}$=3.0 Hz, $J_{1,6}$=4.0 Hz, H-1), 5.21 (dd. 1H. $J_{2,3}$=6.5 Hz, $J_{3,4}$=9.0 Hz, H-3), 4.93 –4.65 (m. 1H, H-4), 4.38 –4.15 (m, 2H, H-5, 6), 3.61 (dd, 1H, H-2), 3.42 (s, 3H, OMe), 2.44 (s, 3H, PhMe), 2.12, 2.05 (2s, each 3H, 2×OAc), 1.50, 1.32 (2s, each 3H, $CMe_2$).
elementary analysis as $C_{21}H_{28}O_{10}S$ (%): C: 53.38, H: 5.97 (calculated). C: 53.24, H: 6.13 (found).
$[\alpha]_D^{18}$: $-70.0°$ (c, 1.72, $CHCl_3$)

b) To compound 17 (380 mg, 0.805 nmol) were added sodium azide (260 mg, 4.03 mmol) and 90% 2-methoxyethanol (4 ml). Reaction was made with refluxing in an oil bath at 125° C. for 14 hours. By toluene-azeotropy, vacuum-concentration of the reaction liquid, compound 18 (0.6 g) was obtained as a brown solid. After addition of pyridine (5 ml) and acetic anhydride (5 ml), stirring was done at room temperature for 14 hours. The reaction liquid was added dropwise to ice water (50 ml) and extracted with ethyl acetate (100 ml). The resulting organic phase was washed with water (twice each 30 ml), followed by drying with sodium sulfate anhydride and by subsequent filtration of the drying agent. In vacuo concentration of the filtrate while in azeotropy with toluene gave a brown syrup (0.3 g). The syrup product was silica gel-chromatographed (ethyl acetate/hexane=1/6) to obtain as a black syrup 1L-1,3-di-O-acetyl-4-azido-4-deoxy-5,6-O-isopropylidene-2-O-methyl-chiro-inositol (compound 19) (270 mg, 98% yield).

compound 19

Rf: 0.39 (ethyl acetate/hexane=⅓, v/v).

IR (neat): 2100 cm$^{-1}$ (N$_3$). 1750 cm$^{-1}$ (OAc).

$^1$H-NMR (δ, 90 MHz, CDCl$_3$): 5.37 (dd, 1H, J$_{1,2}$=3.0 Hz, J$_{1,6}$=5.0 Hz, H-1), 4.91 (dd, 1H, J$_{2,3}$=6.0 Hz, J$_{3,4}$=10.0 Hz, H-3), 4.43 –4.06 (m, 2H, H-5, 6), 3.69 (t, 1H, J$_{4,5}$=10.0 Hz, H-4), 3.50 (dd, 1H, H-2), 3.43 (s, 3H, OMe), 2.14 (s, 6H, 2×OAc), 1.55, 1.37 (2s, each 3H, CMe$_2$).

elementary analysis as C$_{14}$H$_{21}$N$_3$O$_7$ (%): C: 48.98, H: 6.17, N: 12.24 (calculated). C: 48.96, H: 5.91, N: 12.25 (found).

[α]$_D^{20}$: −54.7° (c, 1.79, CHCl$_3$).

c) To compound 19 (118 mg, 0.344 mmol) were added ethanol (3 ml), acetic anhydride (0.27 ml) and Raney nickel-T4 catalyst (an amount of 2 small spatulas). Reaction was made with shaking on a Parr reduction device at an initial pressure of 55 psi for a time length of 32 hours. The reaction liquid was filtered to remove excess catalyst, whereupon the filtrate was vacuum-concentrated by toluene-azeotropy. A green syrup (0.14 g) was obtained which was thereater purified by silica gel chromatography (ethanol/toluene=1/15) to give as a white crystal 1L-4-acetamido-1,3-di-O-acetyl-4-deoxy-5,6-O-isopropylidene-2-O-methyl-chiro-inositol (compound 20) (102 mg, 82% yield). The resulting compound was further recrystallized from ethanol.

compound 20

Rf: 0.42 (ethanol/toluene=1/7, v/v).

mp: 133°–135° C. (ethanol).

IR (neat): 3300 cm$^{-1}$ (NH), 1750 cm$^{-1}$ (OAc), 1660 cm$^{-1}$ (amide), 1550 cm$^{-1}$ (amide).

$^1$H-NMR (δ, 90 MHz, CDCl$_3$): 5.74 (d, 1H, 9.0 Hz, NH), 5.55 (dd, 1H, J$_{1,2}$=3.0 Hz, J$_{1,6}$=4.2 Hz, H-1), 5.02 (dd, 1H, J$_{2,3}$=7.5 Hz, J$_{3,4}$=8.0 Hz, H-3), 4.52 –4.02 (m, 3H, H-4, 5, 6), 3.67 (dd, 1H, H-2), 3.44 (s, 3H, OMe), 2.15, 2.10, 1.97 (3s, each 3H, 3×OAc), 1.56, 1.45 (2s, each 3H, CMe$_2$).

elementary analysis as C$_{16}$H$_{25}$NO$_8$ (%): C: 53.47, H: 7.01, N: 3.90 (calculated). C: 53.24, H: 6.88, N: 3.68 (found).

[α]$_D^{22}$: −54.5° (c, 1.15, CHCl$_3$).

d) Compound 20 (89 mg, 0.247 mmol) after being mixed with 75% acetic acid (1 ml) was reacted at 55° C. for 14 hours. After addition of toluene the reaction liquid was azeotropically concentrated in vacuo. A white solid (82 mg) was obtained which, upon incorporation with pyridine (1 ml) and acetic anhydride (1 ml), was reacted at room temperature for 16 hours. Toluene-azeotropy, vacuum-concentration of the reaction liquid gave a pale yellow syrup (100 mg). Silica gel-chromatographing (ethanol/toluene=⅓) provided as a white solid title compound 21 or ultimate compound B (76 mg, 76% yield). Recovered was compound 20 (15 mg, 17%). Compound 21 was further recrystallized from ethanol.

compound 21 (compound B)

Rf: 0.30 (ethanol/toluene=1/5, v/v).

mp: 157°–158° C. (ethanol).

IR (neat): 3370 cm$^{-1}$ (NH), 3300 cm$^{-1}$ (NH), 1750 cm$^{-1}$ (OAc), 1675 cm$^{-1}$ (amide), 1550 cm$^{-1}$ (amide).

$^1$H-NMR (δ, 90 MHz, CDCl$_3$): 5.66 (d, 1H, J$_3$NH=10.0 Hz, NH), 5.44, 5.30 (2dd, each 1H, J$_{1,2}$=J$_{5,6}$=3.5 Hz, J$_{1,6}$=4.5 Hz, H-4), 4.53 (dt, q-like, 1H, H-3), 3.64 (dd, 1H, H-5), 3.37 (s, 3H, OMe), 2.16, 2.13, 2.08, 2.00, 1.90 (5s, each 3H, NHAc, 4×OAc).

elementary analysis as C$_{17}$H$_{25}$NO$_{10}$ (%): C: 50.62, H: 6.25, N: 3.47 (calculated). C: 50.88, H: 6.09, N: 3.44 (found).

[α]$_D^{21}$: −11.9° (c, 1.06, CHCl$_3$).

EXAMPLE 4

1D-2-acetamido-1,3,4,5-tetra-O-acetyl-2-deoxy-6-O-methyl-chiro-inositol (compound 26) (compound C) and
1L-2-acetamido-1,3,4,6-tetra-O-acetyl-2-deoxy-5-O-methyl-chiro-inositol (compound 27) (compound D)

a) The procedure of item a) of Example 1 was followed in preparing compounds 2 and 3 from L-quebrachitol 1. Compound 2 was likewise extracted into an aqueous phase and compound 3 into an organic phase.

By in vacuo concentration of the aqueous phase while in azeotropy with ethanol, n-butanol and toluene in this order, there was obtained compound 2 as a salt-containing syrup. Desalting was done with use of a short column packed with silica gel. The thus treated syrup after being mixed with pyridine (100 ml) and acetic anhydride (100 ml) was allowed to react with stirring at room temperature for 7 hours. On azeotropic concentration in vacuo and with toluene and subsequent dilution with ethyl acetate, the reaction liquid was filtered to remove salts having been deposited. Toluene-azeotropy, vacuum-concentration of the filtrate yielded a brown syrup which, after addition of 80% acetic acid (20 ml), was stirred in an oil bath at 55° C. for 24 hours. The reaction liquid was azeotropically concentrated in vacuo and with toluene, yielding a brown syrup (8.6 g). Purification by silica gel chromatography (ethyl acetate/toluene=3/2) gave as a white solid 1L-1,3,4-tri-O-acetyl-2-O-methyl-chiro-inositol (compound 22) (5.62 g, 35% yield). The resulting compound was further recrystallized from ethanol.

compound 22

Rf: 0.36 (MEK/toluene=1/1, v/v).

mp: 122°–124° C. (ethanol).

IR (neat): 3470 cm$^{-1}$ (OH), 1750 cm$^{-1}$ (OAc).

$^1$H-NMR (δ, 90 MHz, CDCl$_3$): 5.50 (t, 1H, J=3.5 Hz, H-1), 5.30 –5.05 (m, 2H, H-3, 4), 4.15 –3.50 (m, 4H), 3.47 (s, 3H, OMe), 3.30 –3.10 (m, 1H), 2.13, 2.08, 2.05 (3s, each 3H, 3×OAc).

elementary analysis as C$_{13}$H$_{20}$O$_9$ (%): C: 48.75, H: 6.29 (calculated). C: 48.44, H: 6.12 (found).

[α]$_D^{24}$: −75.4° (c, 1.01, CHCl$_3$).

b) To compound 22 (1.05 g, 3.28 mmol) were added p-toluenesulfonyl chloride (1.25 g, 6.56 mmol) and pyridine (10 ml). Reaction was made with stirring at room temperature for 8 hours. The reaction liquid after being diluted with ethyl acetate (300 ml) was washed with water (twice each 200 ml). After drying with sodium sulfate anhydride, the resulting organic phase was filtered to remove the drying agent. By toluene-azeotropy, vacuum-concentration of the filtrate, a brown syrup (1.9 g) was obtained which was subsequently silica gel-chromatographed (MEK/toluene=1/6) to provide as a colorless syrup 1L-1,3,4-tri-O-acetyl-2-O-methyl-5-O-(p-toluenesulfonyl)chiro-inositol (compound 23) (1.4 g, 90% yield).

compound 23

Rf: 0.44 (MEK/toluene=⅓, v/v).

IR (neat): 3470 cm$^{-1}$ (OH), 1750 cm$^{-1}$ (OAc), 1180 cm$^{-1}$ (SO$_2$), $^1$H-NMR (δ, 90 MHz, CDCl$_3$): 7.80 –7.20 (m, 4H, Ph), 5.54 (t, 1H, $J_{1,2}=J_{1,6}=3.5$ Hz, H-1), 5.42 (t, 1H, $J_{3,4}=J_{4,5}=9.0$ Hz, H-4), 5.19 (t, 1H, $J_{2,3}=9.0$ Hz, H-3), 4.74 (dd, 1H, $J_{5,6}=3.0$ Hz, H-5), 4.24 (ddd, q-like, 1H, $J_{6,OH}=3.2$ Hz, H-6), 3.70 (dd, 1H, H-2), 3.35 (s, 3H, OMe), 2.92 (d, 1H, OH), 2.46 (s, 3H, PhMe), 2.15, 2.01, 1.73 (3s, each 3H, 3×OAc).

elementary analysis as C$_{20}$H$_{26}$O$_{11}$S (%): C: 50.63, H: 5.52 (calculated). C: 50.37, H: 5.83 (found).

8 $[α]_D^{18}$: −66.1° (c, 2.90, CHCl$_3$).

c) Compound 23 (419 mg, 0.883 mmol) was incorporated with sodium azide (230 mg, 3.53 mmol) and 90% 2-methoxyethanol (4 ml). The whole was refluxed in an oil bath at 125° C. for 20 hours. After cooling to room temperature, the reaction liquid was azeotropically vacuum-concentrated with use of toluene to form a brown solid (5.3 g). The solid product after being mixed with pyridine (3 ml) and acetic anhydride (3 ml) was reacted with stirring at room temperature for 23 hours. The resulting liquid was taken dropwise into ice water (30 ml) and extracted with ethyl acetate (70 ml).

The organic phase formed above was washed with water (30 ml) and then dried with sodium sulfate anhydride. Filtration was done to remove the drying agent, and the filtrate was vacuum-concentrated by toluene-azeotropy to obtain a brown syrup (0.37 g). Silica gel-chromatographing (MEK/toluene=1/10) provided as a white solid 1D-1,3,4,5-tetra-O-acetyl-2-azido-2-deoxy-6-O-methyl-chiro-inositol (compound 24) (147 mg, 43% yield) and as a colorless syrup 1L-1,3,4,6,-tetra-O-acetyl-2-azido-2-deoxy-5-O-methyl-chiro-inositol (compound 25) (48 mg, 14% yield). Compound 24 was further recrystallized from ethanol.

compound 24

Rf: 0.34 (MEK/toluene=1/10, v/v).
mp: 83.0°–83.5° C. (ethanol).

IR (neat): 2110 cm$^{-1}$ (N$_3$), 1760 cm$^{-1}$ (OAc), $^1$H-NMR (δ, 90 MHz, CDCl$_3$): 5.50 –5.05 (m, 4H, H-1, 3, 4, 5), 3.94 (dd, 1H, $J_{1,2}=3.4$ Hz, $J_{2,3}=10.2$ Hz, H-2), 3.83 (t, 1H, $J_{1,6}=J_{5,6}=3.3$ Hz, H-6), 3.50 (s, 3H, OMe), 2.12, 2.10, 2.06, 2.00 (4s, each 3H, 4×OAc).

elementary analysis as C$_{15}$H$_{21}$N$_3$O$_9$ (%): C: 46.51, H: 5.46, N: 10.84 (calculated). C: 46.18, H: 5.31, N: 10.77 (found).

$[α]_D^{27}$: +28.9° (c, 1.07, CHCl$_3$).

compound 25

Rf: 0.26 (MEK/toluene=1/10, v/v).
mp: syrup.

IR (neat): 2110 cm$^{-1}$ (N$_3$), 1760 cm$^{-1}$ (OAc).

$^1$H-NMR (δ, 90 MHz, CDCl$_3$): 5.53 –5.20 (m, 4H, H-1, 3, 4, 6), 3.94 (dd, 1H, $J_{1,2}=3.0$ Hz, $J_{2,3}=10.0$ Hz, H-2), 3.62 –3.45 (m, 1H, H-5), 3.35 (s, 3H, OMe), 2.16, 2.15, 2.10, 2.07 (4s, each 3H, 4×OAc).

elementary analysis as C$_{15}$H$_{21}$N$_3$O$_9$ (%): C: 46.51, H: 5.46, N: 10.84 (calculated). C: 47.09, H: 5.38, N: 10.27 (found).

$[α]_D^{23}$: −41.2° (c, 1.37, CHCl$_3$).

d) To compound 24 (147 mg, 0.38 mmol) were added ethanol (6 ml), acetic anhydride (0.2 ml) and Raney nickel-T4 catalyst (an amount of one small spatula). Reaction was made with shaking on a Parr reduction device at an initial pressure of 55 psi for a time length of 39 hours. Excess catalyst was removed by filtration with use of zeolite. A green syrup (0.2 g) was obtained by toluene-azeotropy, vacuum-concentration of the filtrate. The syrup was purified by silica gel chromatography (ethanol/toluene=1/10), thus providing as a colorless syrup title compound 26 or ultimate compound C (89 mg, 58% yield).

compound 26 (compound C)

Rf: 0.25 (ethanol/toluene=1/10, v/v).
mp: syrup.

IR (neat): 3360 cm$^{-1}$ (NH). 3280 cm$^{-1}$ (NH), 1750 cm$^{-1}$ (OAc), 1660 cm$^{-1}$ (amide), 1550 cm$^{-1}$ (amide).

$^1$H-NMR (δ, 270 MHz, CDCl$_3$): 5.65 (d, 1H, $J_{2,NH}=8.8$ Hz, NHAc), 5.50 (t, 1H, $J_{2,3}=J_{3,4}=10.0$ Hz, H-3), 5.26 (t, 1H, $J_{1,2}=J_{1,6}=3.1$ Hz, H-1), 5.13 (t, 1H, $J_{4,5}=10.0$ Hz, H-3), 5.08 (dd, 1H, $J_{5,6}=3.1$ Hz, H-5), 4.66 (ddd, 1H, H-2), 3.74 (t, 1H, H-6), 3.52 (s, 3H, OMe), 2.18, 2.08, 2.04, 2.01, 1.93 (5s, each 3H, NHAc, 4×OAc).

elementary analysis as C$_{17}$H$_{25}$NO$_{10}$ (%): C: 50.63, H: 6.25, N: 3.47 (calculated). C: 50.97, H: 6.18, N: 3.12 (found).

$[α]_D^{21}$: +33.9° (c, 0.72, CHCl$_3$).

e) To compound 25 (96 mg, 0.25 mmol) were added ethanol (3 ml), acetic anhydride (0.13 ml) and Raney nickel-T4 catalyst (an amount of one small spatula). Shaking was effected on a Parr reduction device with 55 psi in initial pressure and 16 hours in time length. By zeolite filtration and azeotropic concentration of the reaction liquid as in compound 24, there was a green syrup (0.12 g). Silica gel-chromatographing (ethanol/toluene=1/10) provided as a white crystal title compound 27 or ultimate compound D (80 mg, 80% yield). The resulting compound was further recrystallized from ethanol.

compound 27 (compound D)

Rf: 0.29 (ethanol/toluene=1/10, v/v).
mp: 193°–194° C. (ethanol).

IR (neat): 3280 cm$^{-1}$ (NH), 1750 cm$^{-1}$ (OAc), 1660 cm$^{-1}$ (amide), 1550 cm$^{-1}$ (amide).

$^1$H-NMR (δ, 90 MHz, CDCl$_3$): 5.73 (d, 1H, $J_{2,NH}=9.0$ Hz, NHAc), 5.50 (t, 1H, $J_{1,6}=J_{5,6}=3.5$ Hz, H-6), 5.27 (t, 1H, $J_{3,4}=J_{4,5}=9.5$ Hz, H-2), 5.17 (t, 1H, $J_{1,2}=3.5$ Hz, H-5), 5.12 (t, 1H, $J_{2,3}=9.5$ Hz, H-3), 4.77–3.96 (m, 1H, H-2), 3.47 (dd, 1H, H-5), 3.35 (s, 3H, OMe), 2.16, 2.06, 2.03, 1.90 (4s, 6H, 3H, 3H, NHAc, 4×OAc).

elementary analysis as C$_{17}$H$_{25}$NO$_{10}$ (%): C: 50.63, H: 6.25, N: 3.47 (calculated). C: 50.45, H: 5.15, N: 3.47 (found).

$[α]_D^{23}$: −33.2° (c, 1.11, CHCl$_3$).

EXAMPLE 5

1D-2,4-diacetamido-1,3,5-tri-O-acetyl-2,4-dideoxy-6-O-methyl-chiro-inositol (compound 33) (compound E),
1D-1,2-diacetamido-4,5,6-tri-O-acetyl-1,2-dideoxy-3-O-methyl-chiro-inositol (compound 34) (compound F)
and
1L-3-acetamido-1,2,4,6-tetra-O-acetyl-3-deoxy-5-O-methyl-muco-inositol (compound 35) (compound G)

a) The procedure of item a) of Example 1 was followed in preparing compound 28 from L-quebrachitol 1 via compounds 2 and 3. Compound 28 was the same as compound 22 obtained in item a) of Example 4.

b) Compound 28 (1.00 g, 3.13 mmol) was dissolved in pyridine (10 ml) and thereafter incorporated dropwise with ice cooling with methanesulfonyl chloride (0.97 ml, 12.5 mmol). Reaction was made with stirring at 0° C. for 15 minutes and at room temperature for 13 hours. The reaction liquid after being diluted with ethyl acetate (50 ml) was put by stepwise droping into ice water (200 ml) and extracted with ethyl acetate (100 ml). The resulting organic phase was washed with water (100 ml) and dried with sodium sulfate anhydride, followed by filtration to remove the drying agent. With addition of toluene the filtrate was azeotropically concentrated in vacuo, thereby yielding a foamy brown syrup (1.5 g). The syrup product was silica gel-chromatographed (MEK/toluene=$\frac{1}{2}$) to provide as a colorless syrup 1L-1,3,4-tri-O-acetyl-5,6-di-O-methanesulfonyl-2-O-methyl-chiro-inositol (compound 29) (1.35 g, 91% yield).

compound 29

Rf: 0.42 (MEK/toluene=1/2, v/v).
IR (neat): 1750 cm$^{-1}$ (OAc), 1180 cm$^{-1}$ (SO$_2$),
$^1$H-NMR ($\delta$, 90 MHz, CDCl$_3$): 5.65 (t, J$_{1.6}$=J$_{5.6}$=3.2 Hz, H-6), 5.55–4.90 (m, 4H, H-1, 2, 3, 4), 3.77–3.60 (m, 1H, H-5), 3.47 (s, 3H, OMe), 3.18, 3.08 (2s, each 3H, 2×OMs), 2.18, 2.08, 2.07 (3s, each 3H, 3×OAc).
elementary analysis as C$_{15}$H$_{24}$O$_{13}$S$_2$ (%): C: 37.80, H: 5.08, S : 13.46 (calculated). C: 37.51, H: 4.91 (found).
[$\alpha$]$_D^{27}$: −51.3° (c, 1.03, CHCl$_3$).

c) To compound 29 (505 mg, 1.06 mmol) were added sodium azide (690 mg, 10.6 mmol) and aqueous 90% 2-methoxyethanol (5 ml). Reaction was made with refluxing in an oil bath at 125° C. for 6 hours. On cooling to room temperature, the reaction liquid was azeotropically vacuum-concentrated with toluene to obtain a brown solid (1.1 g) which, after being incorporated with pyridine (5 ml) and acetic anhydride (5 ml), was reacted at room temperature for 5 hours. After completion of the reaction, dilution was done with ethyl acetate (70 ml) and washing with water (3 times each 40 ml).

The resulting organic phase was dried with sodium sulfate anhydrate, followed by filtration to remove the drying agent. A brown syrup (0.38 g) was obtained by toluene-azeotropy, vacuum-concentration of the filtrate. The syrup was silica gel-chromatographed (ethyl acetate/hexane=$\frac{1}{4}$ to $\frac{1}{3}$) to provide a colorless syrup 1D-1,3,5-tri-O-acetyl-2,4-diazido-2,4-dideoxy-6-O-methyl-chiro-inositol (compound 30) (165 mg, 42% yield), as a colorless syrup 1D-1,2,3-tri-O-acetyl-5,6-diazido-5,6-dideoxy-4-O-methyl-chiro-inositol (compound 31) (48 mg, 12% yield) and as a white solid 1D-2,4,5,6-tetra-O-acetyl-3-azido-3-deoxy-1-O-methyl-muco-inositol (compound 32) (25 mg, 6% yield). Compound 32 was further recrystallized from ethanol.

compound 30

Rf: 0.41 (ethyl acetate/hexane=$\frac{1}{4}$, v/v).
mp: syrup.
IR (neat): 2110 cm$^{-1}$ (N$_3$), 1760 cm$^{-1}$ (OAc).
$^1$H-NMR ($\delta$, 90 MHz, CDCl$_3$): 5.48 (t, 1H, J$_{1.2}$=J$_{1.6}$=3.8 Hz, H-1), 5.22 (t, 1H, J$_{2.3}$=J$_{3.4}$=10.0 Hz, H-3), 4.97 (dd, 1H, J$_{4.5}$=10.0 Hz, J$_{5.6}$=3.0 Hz, H-5), 3.92 (t, 1H, H-4), 3.75 (dd, 1H, H-2), 3.72 (t, 1H, H-6), 3.50 (s, 3H, OMe), 2.19, 2.15 (2s, 3H, 6H, 3×OAc).
elementary analysis as C$_{13}$H$_{18}$N$_6$O$_7$ (%): C: 42.16, H: 4.90, N: 22.69 (calculated). C: 41.99, H: 4.91, N: 23.04 (found).
[$\alpha$]$_D^{25}$: +21.9° (c, 0.87, CHCl$_3$).

compound 31

Rf: 0.34 (ethyl acetate/hexane=$\frac{1}{4}$, v/v).
mp: syrup.
IR (neat): 2120 cm$^{-1}$ (N$_3$), 1760 cm$^{-1}$ (OAc).
$^1$H-NMR ($\delta$, 270 MHz, CDCl$_3$): 5.32 (t, 1H, J$_{1.6}$=J$_{5.6}$=3.3 Hz, H-6) 5.30 (dd, 1H, J$_{4.5}$=10.3 Hz, J$_{3.4}$=9.5 Hz, H-4) 5.09 (dd, 1H, H-5) 3.90 (t, 1H, J$_{1.2}$=9.5 Hz, J$_{5.6}$=3.3 Hz, H-2) 3.87 (t, 1H, H-1) 3.60 (t, 1H, H-4) 3.60 (s, 3H, OMe), 2.15, 2.10, 1.98 (3s, each 3H, 3×OAc).
elementary analysis as C$_{13}$H$_{18}$N$_6$O$_7$ (%): C: 42.16, H: 4.90, N: 22.69 (calculated). C: 41.96, H: 4.76, N: 22.65 (found).
[$\alpha$]$_D^{21}$: −23.0° (c, 1.76, CHCl$_3$).

compound 32

Rf: 0.21 (ethyl acetate/hexane=$\frac{1}{4}$, v/v). mp: 76°–80° C. (ethanol).
IR (neat): 2120 cm$^{-1}$ (N$_3$), 1750 cm$^{-1}$ (OAc).
$^1$H-NMR ($\delta$, 90 MHz, CDCl$_3$): 5.40–4.90 (m, 4H, H-2, 4, 5, 6), 4.20 (t, 1H, J$_{2.3}$=J$_{3.4}$=9.0 Hz, H-3), 3.60 (td, 1H, J$_{1.2}$=J$_{1.6}$=3.5 Hz, J1.5=1.5 Hz, H-1), 3.44 (s, 3H, OMe), 2.19, 2.15, 2.12, 2.08 (4s, each 3H, 4×OAc).
elementary analysis as C$_{15}$H$_{21}$N$_3$O$_9$ (%): C: 46.51, H: 5.46, N: 10.84 (calculated). C: 46.13, H: 5.32, N: 11.08 (found).
[$\alpha$]$_D^{27}$: +11.8° (c, 1.00, CHCl$_3$).

d) To compound 30 (209 mg, 0.564 mmol) were added ethanol (10 ml), acetic anhydride (0.90 ml) and Raney nickel-T4 catalyst (an amount of 3 small spatulas). Shaking was carried out on a Parr reduction device with 55 psi in initial pressure and 72 hours in time length. On completion of the reaction, residual catalyst was removed by filtration on zeolite. The filtrate was concentrated in vacuo and by azeotropy with toluene so that a green syrup (0.3 g) was obtained which was thereafter silica gel-chromatographed (ethanol/toluene=$\frac{1}{4}$) to provide as a white crystalline solid title compound 33 or ultimate compound E (159 mg, 70% yield). The resulting compound was further recrystallized from ethanol and chloroform.

compound 33 (compound E)

Rf: 0.33 (ethanol/toluene=$\frac{1}{4}$, v/v).
mp: 243°–245° C. (ethanol and chloroform).
IR (neat): 3250 cm$^{-1}$ (NH), 1740 cm$^{-1}$ (OAc), 1650 cm$^{-1}$ (amide), 1550 cm$^{-1}$ (amide).
$^1$H-NMR ($\delta$, 90 MHz, CDCl$_3$): 5.77, 5.58 (2d, each 1H, J$_{2.NH}$=J$_{4.NH}$=9.0 Hz, 2×NHAc), 5.25 (t, 1H, J$_{1.2}$=J$_{1.6}$=3.5 Hz, H-1), 5.17–4.88 (m, 2H, H-3, 5), 4.83–4.53 (m, 2H, H-2, 4), 3.67 (dd, 1H, J$_{5.6}$=3.0 Hz, H-6), 3.55 (s, 3H, OMe), 2.16, 2.10, 2.05, 1.93, 1.90 (5s, each 3H, 2×NHAc, 3×OAc).

elementary analysis as $C_{17}H_{26}N_2O_9 \cdot \frac{1}{2}H_2O$ (%): C: 49.63, H: 6.62, N: 6.81 (calculated). C: 49.96, H: 6.50, N: 6.73 (found).

$[\alpha]_D^{24}$: +25.4° (c, 1.28, $CH_3OH$).

e) Compound 31 (107 mg, 0.289 mmol) was incorporated with ethanol (6 ml), acetic anhydride (0.3 ml) and Raney nickel-T4 catalyst (an amount of one small spatula). Reaction was made with shaking on a Parr reduction device with 55 psi in initial pressure and 22 hours in time length. The reaction liquid was treated as was in compound 30, whereby a green syrup (0.17 g) was formed. The syrup product was silica gel-chromatographed (ethanol/toluene=$\frac{1}{4}$) to provide as a colorless syrup title compound 34 or ultimate compound F (84 mg, 72% yield). The resulting compound was further recrystallized from ethanol and chloroform.

compound 34 (compound F).

Rf: 0.32 (ethanol/toluene=$\frac{1}{4}$, v/v).

mp: 137°-140° C. (ethanol and chloroform).

IR (neat): 3280 $cm^{-1}$ (NH), 1750 $cm^{-1}$ (OAc), 1660 $cm^{-1}$ (amide), 1550 $cm^{-1}$ (amide).

$^1$H-NMR ($\delta$, 270 MHz, $CD_3OD$): 5.35 (dd, 1H, $J_{3,4}$=9.89 Hz, $J_{4,5}$=9.16 Hz, H-4), 5.23 (dd, 1H, $J_{5,6}$=3.30 Hz, H-5), 5.19 (t, 1H, $J_{1,6}$=3.30 Hz, H-6), 4.84 (s, 3H, OMe), 4.45 (dd, 1H, $J_{1,2}$=4.77 Hz, H-1), 4.41 (dd, 1H, $J_{2,3}$=11.00 Hz, H-2), 3.56 (dd, 1H, H-3), 2.16, 2.08, 2.05, 1.94 (4s, 3H, 3H, 3H, 6H, 2×NHAc, 3×OAc).

elementary analysis as $C_{17}H_{26}N_2O_9 \cdot \frac{1}{2}H_2O$ (%): C: 49.63, H: 6.62, N: 6.81 (calculated). C: 50.07, H: 6.28, N: 6.96 (found).

$[\alpha]_D^{24}$: +17.1° (c, 0.76, $CH_3OH$).

f) To compound 32 (120 mg, 0.310 mmol) were added ethanol (2 ml), acetic anhydride (0.15 ml) and Raney nickel-T4 catalyst (an amount of 3 small spatulas). The mixture was subjected to shaking on a Parr reduction device with 55 psi in initial pressure and 14 hours in time length. A green syrup (0.16 g) was obtained by treatment of the reaction liquid as in compound 30. Subsequent purification by silica gel chromatography (ethanol/toluene=1/9) gave as a colorless syrup title compound 35 or ultimate compound G (114 mg, 91% yield). The resulting compound was further recrystallized from ethanol.

compound 35 (compound G)

Rf: 0.27 (ethanol/toluene=$\frac{1}{4}$, v/v).

mp: 161°-162° C. (ethanol).

IR (neat): 3300 $cm^{-1}$ (NH), 1750 $cm^{-1}$ (OAc), 1660 $cm^{-1}$ (amide), 1550 cm-I (amide).

$^1$H-NMR ($\delta$, 270 MHz, $CD_3Cl$): 5.40 (bd, 1H, $J_{3,NH}$=9.89 Hz, NHAc), 5.30 (t, 1H, J-3.30 Hz, H-5 or 6), 5.06 (dd, 1H, J-10.26 Hz, J-3.30 Hz, H-2 or 4), 4.86 (dt, q-like, 1H, J=9.89 Hz, H-3), 3.47 (s, 3H, OMe), 3.30 (t, 1H, J=3.61 Hz, H-5), 2.13, 2.11, 2.03, 1.92 (4s, 6H, 3H, 3H, 3H, NHAc, 4×OAc).

elementary analysis as $C_{17}H_{25}NO_{10}$ (%): C: 50.63, H: 6.25, N: 3.47 (calculated). C: 50.69, H: 6.08, N: 3.30 (found).

$[\alpha]_D^{21}$: +5.4° (c, 1.46, $CHCl_3$).

EXAMPLE 6

1L-1-acetamido-2,3,4,6-tetra-O-acetyl-1-deoxy-5-O-methyl-chiro-inositol (compound 42) (compound H)

and 1D-1-acetamido-3,4,5,6-tetra-O-acetyl-1-deoxy-2-O-methyl-scyllo-inositol (compound 43) (compound I)

a) The procedure of item a) of Example 1 was followed in preparing compounds 2 and 3 from L-quebrachitol 1. Compound 2 was likewise extracted into an aqueous phase and compound 3 into an organic phase.

b) The aqueous phase in item a) above was condensed in vacuo and by azeotropy with ethanol, n-butanol and toluene in this order, thereby obtaining compound 2 as a syrup. After addition of pyridine (100 ml) and acetic anhydride (100 ml) to the syrup, reaction was made at room temperature for 7 hours. The reaction liquid was azeotropically concentrated in vacuo and with toluene, followed by dilution with ethyl acetate and by subsequent filtration to remove salts diposited. Similar azeotropic concentration of the filtrate gave as a brown syrup 1L-1,3,4-tri-O-acetyl-5,6-O-isopropylidene-2-O-methyl-chiro-inositol (compound 36) (10.8 g yield). The syrup after being incorporated with 80% acetic acid (20 ml) was reacted with stirring in an oil bath at 55° C. for 24 hours. A brown syrup was derived by concentrating the reaction liquid in vacuo and with toluene and silica gel-chromatographed (ethyl acetate/toluene=3/2) to give as a white solid 1L-1,3,4-tri-O-acetyl-2-O-methyl-chiro-inositol (compound 38) (5.62 g, 34% yield based on compound 1).

c) The organic phase in item a) above was dried with sodium sulfate anhydride. On removal of the drying agent by filtration and vacuum concentration of the filtrate, there was obtained as a pale yellow syrup compound 3 (6.9 g) which, after addition of pyridine (50 ml) and acetic anhydride (50 ml), was reacted at room temperature for 26 hours. Toluene-azeotropy, vacuum-concentration of the reaction liquid gave a brown crude crystal (7.54 g) which, on recrystallization from ethanol, provided 1L-1-O-acetyl-3,4:5,6-di-O-isopropylidene-2-O-methyl-chiro-inositol (compound 37) (5.39 g, 33% yield based on compound 1).

Compound 37 was reacted, with addition of 67% acetic acid (3 ml), with stirring at room temperature for 2 hours. A white syrup (103 mg) resulted from azeotropic concentration of the reaction liquid in vacuo and with toluene. With pyridine (1 ml) and acetic anhydride (1 ml) added to the syrup, reaction was continued with stirring at room temperature for 3 hours. Dilution was thereafter done with ethyl acetate (50 ml) and washing with water (twice each 15 ml). The resulting organic phase was dried with sodium sulfate anhydride and filtered to remove the drying agent. A colorless syrup (138 mg) was obtained after the filtrate had been condensed in vacuum.

The colorless syrup derived above was reacted with 67% acetic acid (3 ml) in an oil bath at 60° C. for 12 hours. A colorless syrup (124 mg) was formed from azeotropic concentration of the reaction liquid in vacuo and with toluene. The syrup product was dissolved in ethanol (a small amount), followed by ice cooling and by subsequent addition of hexane (about 2 ml) and a seed crystal. Vigorous stimulation using a micro spatula gave as a white crystal 1L-1,3,4-tri-O-acetyl-2-O-methyl-chiro-inositol (compound 38) (51 mg, 45% yield).

As evidenced by the reaction routes in items b) and c) above, compound 38 has been found derivable from compounds 2 and 3 separated into aqueous and organic phases.

d) To compound 38 (152 mg, 0.475 mmol) were added pyridine (1.5 ml) and benzoyl chloride (55 μl, 0.475 mmol). Reaction was made with stirring at room temperature for 2 hours and continued, with further addition of methanesulfonyl chloride (184 μl, 2.375 mmol), at the same temperature for 15 hours. The reaction liquid after being diluted with ethyl acetate was filtered to remove insoluble matter, whereupon the filtrate was concentrated in vacuo. The steps from dilution to condensation were repeated to form a pale yellow foamy syrup (250 mg). On purifying the syrup by silica gel chromatography (ethyl acetate/toluene=1), there was provided 1L-3,4,6-tri-O-acetyl-2-O-benzoyl-1-O-methylsulfonyl-5-O-methyl-chiro-inositol (compound 39) (196 mg, 82% yield).

compound 39.

Rf: 0.42 (toluene/ethanol=15/1, v/v).

IR (neat): 1750 cm$^{-1}$ (OAc, OBz), 1180 cm$^{-1}$ (SO$_2$).

$^1$H-NMR (δ, 90 MHz, CDCl$_3$): 8.2–7.2 (m, 4H, Ph), 3.68 (dd, 1H, J$_{1,6}$=4.5 Hz, J$_{5,6}$=3.5 Hz, H-6), 5.60–5.19 (m, 4H, H-1, 2, 3, 4), 3.73 (dd, 1H, J$_{4,5}$=9.0 Hz, H-5), 3.41 (s, 3H, OMe), 3.00 (s, 3H, OMs). 2.23, 2.10, 1.96 (3s, each 3H, 3×OAc).

elementary analysis as C$_{21}$H$_{26}$O$_{12}$S (%): C: 50.20, H: 5.22 (calculated). C: 49.86, H: 5.45 (found).

[α]$_D^{26}$: −49° (c, 0.92, CHCl$_3$).

e) Compound 39 (176 mg, 0.350 mmol) was reacted with refluxing, with addition of sodium azide (111 mg, 1.71 mmol) and aqueous 90% 2-methoxyethanol (2 ml), in an oil bath at 120° C. for 13 hours. A brown solid (0.17 g) was obtained by azeotropic concentration of the reaction liquid in vacuo and with toluene. With pyridine (1 ml) and acetic anhydride (1 ml) added to the solid product, reaction was continued overnight with stirring at room temperature. Similar concentration was done, followed by dilution with ethyl acetate and by subsequent filtration to remove insoluble matter. The filtrate was vacuum-concentrated to form a brown syrup (0.15 g). Purification by silica gel chromatography (toluene/ethyl acetate=7/1) gave 1L-2,3,4,6-tetra-O-acetyl-1-azido-1-deoxy-5-O-methyl-chiro-inositol (compound 40) (69 mg, 51% yield) and 1D-3,4,5,6-tetra-O-acetyl-1-azido-1-deoxy-2-O-methyl-scyllo-inositol (compound 41) (37 mg, 27% yield).

compound 40

Rf: 0.26 (toluene/ethyl acetate=5/1, v/v).

IR (neat): 2100 cm$^{-1}$ (N$_3$), 1750 cm$^{-1}$ (OAc).

$^1$H-NMR (δ, 90 MHz, CDCl$_3$): 5.50–5.10 (m, 4H, H-2, 3, 4, 6), 4.12 (dd, 1H, J=4.0 Hz, J=3.0 Hz, H-1), 3.65–3.40 (m, 1H, H-5), 3.35 (s, 3H, OMe), 2.16, 2.09, 2.05, 2.02 (4s, each 3H, 4×OAc).

elementary analysis as C$_{15}$H$_{21}$N$_3$O$_9$ (%): C: 46.51, H: 5.46, N: 10.84 (calculated). C: 46.56, H: 5.35, N: 10.58 (found).

[α]$_D^{21}$: −6.0° (c, 0.48, CHCl$_3$).

compound 41

Rf: 0.30 (toluene/ethyl acetate=5/1, v/v).

mp: 128°–130° C. (ethanol).

IR (neat): 2100 cm$^{-1}$ (N$_3$), 1750 cm$^{-1}$ (OAc).

$^1$H-NMR (δ, 90 MHz, CDCl$_3$): 5.25–4.80 (m, 4H, H-3, 4, 5, 6), 3.70–3.15 (m, 2H, H-1, 2), 3.57 (s, 3H, OMe), 2.10, 2.08, 1.99 (3s, 3H, 3H, 6H, 4×OAc).

elementary analysis as C$_{15}$H$_{21}$N$_3$O$_9$ (%): C: 46.51, H: 5.46, N: 10.84 (calculated). C: 46.58, H: 5.22, N: 10.56 (found).

[α]$_D^{27}$: −14.0° (c, 0.91, CHCl$_3$).

f) To compound 40 (27 mg, 70 μmol were added ethanol (1 ml), acetic anhydride (0.2 ml) and Raney nickel-T4 catalyst (an amount of one small spatula). Reaction was made with stirring in a hydrogen atmosphere at one atm for 15 hours. Residual catalyst was removed by filtration from the reaction liquid, after which silica gel-chromatographing was effected to obtain as a syrup title compound 42 or ultimate compound H (21 mg, 74% yield).

compound 42

Rf: 0.42 (toluene/ethanol=5/1, v/v).

mp: syrup.

IR (neat): 3300 cm$^{-1}$ (NH), 3000 cm$^{-1}$ (OH), 1750 cm$^{-1}$ (OAc), 1650 cm$^{-1}$ (amide), 1550 cm$^{-1}$ (amide).

$^1$H-NMR (δ, 90 MHz, CDCl$_3$): 6.00 (d, 1H, J$_{1,NH}$=7.5 Hz, NH), 5.65 (dd, 1H, J=5.0 Hz, J=3.0 Hz, H-6), 5.45–5.00 (m, 3H, H-2, 3, 4), 4.70–4.45 (m, 1H, H-1), 3.65–3.40 (m, 1H, H-5), 3.47 (s, 3H, OMe), 2.15, 2.06, 2.05 (3s, 3H, 6H, 3H, 4×OAc).

elementary analysis as C$_{17}$H$_{25}$NO$_{10}$ (%): C: 50.62, H: 6.25, N: 3.47 (calculated). C: 50.64, H: 6.19, N: 3.42 (found).

[α]$_D^{32}$: −9° (c, 0.98, CHCl$_3$).

g) To compound 41 (24 mg, 62 μmol) were added ethanol (1 ml), acetic anhydride (0.2 ml) and Raney nickel-T4 catalyst (an amount of one small spatula). The mixture was stirred in a hydrogen atmosphere at one atm for 14 hours. By removal of residual catalyst by filtration and by subsequent purification by silica gel chromatography, there was provided as a white solid title compound 43 or ultimate compound I (20 mg, 80% yield).

compound 43 (compound I)

Rf: 0.42 (toluene/ethanol=5/1, v/v).

mp: 215°–216° C. (chloroform).

IR (neat): 3300 cm$^{-1}$ (NH), 1750 cm$^{-1}$ (OAc), 1650 cm$^{-1}$ (amide), 1550 cm$^{-1}$ (amide).

$^1$H-NMR (δ, 270 MHz, CDCl$_3$): 6.00 (d, 1H, J$_{1,NH}$=10.0 Hz, NH), 5.28–5.12 (m, 4H, H-3, 4, 5, 6), 4.15 (dt, J$_{1,2}$=J$_{1,6}$=J$_{1,NH}$=10.0 Hz, H-1), 3.61 (t, 1H, J$_{2,3}$=10.0 Hz, H-2), 3.42 (s, 3H, OMe), 2.07, 2.04, 2.00, 1.98 (4s, each 3H, 4×OAc).

elementary analysis as C$_{17}$H$_{25}$NO$_{10}$ (%): C: 50.62, H: 6.25, N: 3.47 (calculated). C: 50.72, H: 6.16, N: 3.49 (found).

[α]$_D^{21}$: +13 5° (c, 0.17, CHCl$_3$).

EXAMPLE 7

1L-1-acetamido-3,4,5,6-tetra-O-acetyl-1-deoxy-2-O-methyl-chiro-inositol (compound 47) (compound J) and 1L-1-acetamido-2,4,5,6-tetra-O-acetyl-1-deoxy-3-O-methyl-scyllo-inositol (compound 48) (compound K)

a) The procedure item a) of Example 1 was followed in preparing compounds 2 and 3 from L-quebrachitol 1. Compound 2 was likewise extracted into an aqueous phase and compound 3 into an organic phase.

b) The organic phase in item a) above was dried with sodium sulfate anhydride and then filtered to remove the drying agent. Compound 3 was obtained as a pale yellow syrup by azeotropically concentrating the filtrate in vacuo and with toluene. The syrup was treated with petroleum ether into crystalline form. Compound 3 (325 mg, 1.18 mmol) after being mixed with pyridine (2 ml) and methanesulfonyl chloride (183 μl, 2.36 mmol) was reacted with stirring at room temperature for 15 hours. Ethyl acetate (30 ml) was added to dilute the reaction liquid which was thereafter washed with water (10 ml) and dried with sodium sulfate anhydride. A pale yellow syrup was derived upon removal of the drying agent by filtration.

The last-mentioned syrup was incorporated with ethanol (1 ml) and 1M hydrochloric acid (4 ml). Stirring was done in an oil bath at 50° C. for one hour. Upon toluene-azeotropy, vacuum-concentration of the reaction liquid, the residue after being mixed with pyridine (5 ml) and acetic anhydride (5 ml) was reacted with stirring at room temperature for 3 hours. A residue (0.57 g) obtained by similar concentration was silica gel-chromatographed (toluene/MEK=4/1) to give 1L-3,4,5,6-tetra-O-acetyl-1-O-methylsulfonyl-2-O-methyl-chiro-inositol (compound 44) (467 mg, 90% yield).

compound 44

Rf: 0.37 (toluene/MEK=3/1, v/v).
mp: syrup.
IR (neat): 1750 cm$^{-1}$ (OAc), 1175 cm$^{-1}$ (SO$_2$).
$^1$H-NMR ($\delta$, 90 MHz, CDCl$_3$): 5.63-5.50 (m, 1H, H-6), 5.45-5.20 (m, 3H, H-3, 4, 5), 5.08 (dd, 1H, J=3.5 Hz, J=5.0 Hz, H-1), 3.76-3.54 (m, 1H, H-2), 3.48 (s, 3H, OMe), 3.20 (s, 3H, OMs), 2.17, 2.08, 2.02, 1.98 (4s, each 3H, 4×OAc).
elementary analysis as C$_{16}$H$_{24}$O$_{12}$S(%): C: 43.63, H: 5.49 (calculated). C: 43.33, H: 5.15 (found).
$[\alpha]_D^{26}$: $-27°$ (c, 1.35, CHCl$_3$).

c) To compound 44 (485 mg, 1.10 mmol) were added sodium azide (354 mg, 5.45 mmol) and aqueous 90% 2-methoxyethanol (5 ml). Reaction was made with refluxing in an oil bath at 120° C. for 13 hours. From azeotropic concentration of the reaction liquid in vacuo and with toluene, a brown solid was derived which, after addition of pyridine (5 ml) and acetic anhydride (5 ml), was reacted with stirring at room temperature for 3 hours. Similar concentration was done on completion of the reaction, and the residue was diluted with ethyl acetate and filtered to remove insoluble matter. A brown syrup (0.45 g) was obtained by concentrating the filtrate in vacuo. The syrup was silica gel-chromatographed (toluene/ethyl acetate=6/1) to give 1L-3,4,5,6-tetra-O-acetyl-1-deoxy-2-O-methyl-chiro-inositol (compound 45) (290 mg, 68% yield) and 1L-2,4,5,6-tetra-O-acetyl-1-azido-1-deoxy-3-O-methyl-scyllo-inositol (compound 46) (16 mg, 4% yield).

compound 45

Rf: 0.33 (toluene/ethyl acetate=5/1, v/v).
mp: syrup.
IR (neat): 2100 cm$^{-1}$ (N$_3$). 1750 cm$^{-1}$ (OAc).
$^1$H-NMR ($\delta$, 90 MHz, CDCl$_3$): 5.55 -5.00 (m, 4H, H-3, 4, 5, 6), 4.12 (t, 1H, J$_{1.2}$=J$_{1.6}$=4.0 Hz, H-1), 3.61 (dd, 1H, J$_{2.3}$=9.0 Hz, H-2), 3.49 (s, 3H, OMe), 2.16, 2.07, 2.02, 1.97 (4s, each 3H, 4×OAc).
elementary analysis as C$_{15}$H$_{21}$N$_3$O$_9$ (%): C: 46.51, H: 5.46, N: 10.84 (calculated). C: 46.73, H: 5.45, N: 10.47 (found).
$[\alpha]_D^{21}$: $-14.4°$ (c, 0.44, CHCl$_3$).

compound 46

Rf: 0.34 (toluene/ethyl acetate=5/1, v/v).
mp: 144°-145° C. (ethanol).

IR (neat): 2100 cm$^{-1}$ (N$_3$), 1750 cm$^{-1}$ (OAc).
$^1$H-NMR ($\delta$, 90 MHz, CDCl$_3$): 5.23-4.93 (m, 4H, H-2, 4, 5, 6), 3.73-3.30 (m, 1H, H-3), 3.42 (s, 3H, OMe), 2.17, 2.08, 2.06, 2.00 (4s, each 3H, 4×OAc)
elementary analysis as C$_{15}$H$_{21}$N$_3$O$_9$ (%): C: 46.51, H: 5.46, N: 10.84 (calculated). C: 46.73, H: 5.45, N: 10.47 (found).
$[\alpha]_D^{26}$: $-9°$ (c, 0.78, CHCl$_3$)

d) Compound 45 (157 mg, 0.405 mmol) was incorporated with acetic acid (0.2 ml) and Raney nickel-T4 catalyst (an amount of one small spatula). The mixture was reacted with stirring in a hydrogen atmosphere at one atm for 6 hours. Filtration was done to remove residual catalyst. The filtrate was purified by silica gel chromatography (toluene/ethanol=5/1), whereby there was provided as a white solid title compound 47 or ultimate compound J (152 mg, 93% yield).

compound 47 (compound J)

Rf: 0.47 (toluene/ethanol=5/1, v/v).
mp: 183°-184° C. (chloroform).
IR (neat): 3300 cm$^{-1}$ (NH), 1750 cm$^{-1}$ (OAc), 1650 cm$^{-1}$ (amide), 1550 cm$^{-1}$ (amide).
$^1$H-NMR ($\delta$, 90 MHz, CDCl$_3$): 6.09 (d, 1H, J$_{1,NH}$=8.0 Hz, NH), 5.65-5.50 (m, 1H, H-6), 5.38-5.06 (m, 3H, H-3, 4, 5), 4.73-4.48 (m, 1H, H-1), 3.80-3.60 (m, 1H, H-1), 3.47 (s, 3H, OMe), 2.12, 2.10, 2.04, 2.03 (4s, 3H, 3H, 3H, 6H, 4×OAc, NHAc).
elementary analysis as C$_{17}$H$_{25}$NO$_{10}$ (%): C: 50.62, H: 6.25, N: 3.47 (calculated). C: 50.40, H: 5.93, N: 3.48 (found).
$[\alpha]_D^{21}$: $-10.5°$ (c, 1.04, CHCl$_3$).

e) To compound 46 (12 mg, 31 μmol) were added acetic anhydride (0.2 ml) and Raney nickel-T4 catalyst (an amount of one small spatula). Reaction was made in a hydrogen atmosphere at one atm for 10 hours. Residual catalyst on completion of the reaction was removed by filtration. Subsequent purification by silica gel chromatography (toluene/ethanol=5/1) provided as a white solid title compound 48 or ultimate compound K (8 mg, 64% yield).

compound 48 (compound K)

Rf: 0.39 (toluene/ethanol=5/1, v/v).
mp: 206°-208° C. (chloroform).
IR (neat): 3260 cm$^{-1}$ (NH), 3230 cm$^{-1}$ (NH), 1750 cm$^{-1}$ (OAc), 1660 cm$^{-1}$ (amide), 1570 cm$^{-1}$ (amide).
$^1$H-NMR ($\delta$, 90 MHz, CDCl$_3$): 5.66 (d, 1H, J$_{1,NH}$=10.0 Hz, NH), 5.25-4.83 (m, 4H, H-2, 4, 5, 6), 4.31 (q, 1H, J$_{1,2}$=J$_{1.6}$=10.0 Hz, H-1), 3.62-3.46 (m, 1H, H-3), 3.45 (s, 3H, OMe), 2.09, 2.07, 2.01, 2.00, 1.88 (5s, each 3H 4×OAc, NHAc).
elementary analysis as C$_{17}$H$_{25}$NO$_{10}$ (%): C: 50.62, H: 6.25, N: 3.47 (calculated). C: 50.84, H: 6.25, N: 3.46 (found).
$[\alpha]_D^{21}$: $-3.4°$ (c, 0.26, CHCl$_3$).

EXAMPLE 8

1D-acetamido-1,4,5,6-tetra-O-acetyl-2-deoxy-3-O-methyl-allo-inositol (compound 52) (compound L)

a) The reaction steps of items a) and b) of Example 1 were followed in preparing from L-quebrachitol 1 a pale-yellow, syrup-like mixture (18.5 g) of compounds 6, 15 and 49 via compounds 3, 4 and 5. By treatment of the mixture as in the compound 6-compound 15 combination, a syrupy mixture (18.8 g) of compounds 7, 16 and 50 which was subsequently purified in like manner to isolate as a formy syrup compound 7 (4.79 g, 31% yield based on compound 4).

b) From compound 7 were led compound 8 (3.66 g, 64% yield), compound 9 (272 mg, 57% yield) and compound 13 (66 mg, 13% yield) under the same reaction and purification conditions as employed in items c) to e) of Example 1.

c) Compound 13 was converted to compound 14 (19 mg, 80% yield) as in item f) of Example 1. To compound 14 (44 mg, 0.128 mmol) were added ethanol (1 ml), acetic anhydride (0.1 ml) and Raney nickel-T4 catalyst (an amount of one small spatula), and the mixture was stirred in a hydrogen atmosphere at one atom for 2 hours. Upon removal of residual catalyst from the reaction liquid by filtration, azeotropic concentration was carried out in vacuo and with toluene, whereby a colorless syrup (48 mg) was obtained. Silica gel chromatographing (ethanol/toluene=1/12) gave as a colorless syrup 1D-acetamido-1,4-di-O-acetyl-2-deoxy-5,6-O-isopropylidene-3-O-methyl-allo-inositol (compound 51) (37 mg, 81% yield).

compound 51

Rf: 0.36 (ethanol/toluene=1/6, v/v).
mp: syrup.
IR (neat): 3300 cm$^{-1}$ (NH), 1750 cm$^{-1}$ (OAc), 1660 cm$^{-1}$ (amide), 1525 cm$^{-1}$ (amide).
$^1$H-NMR ($\delta$, 90 MHz, CDCl$_3$): 6.07 (d, 1H, $J_{2,NH}$=9.0 Hz, NH), 4.97 (dd, 1H $J_{3,4}$=3.0 Hz, $J_{4,5}$=4.5 Hz, H-4), 5.07 (dd, 1H, $J_{1,2}$=4.0 Hz, $J_{1,6}$=5.0 Hz, H-1), 4.75 (ddd, 1H, $J_{2,3}$=3.0 Hz, H-2), 4.47–4.12 (m, 2H, H-5, 6), 3.70 (t, 1H, H-3), 3.42 (s, 3H, OMe), 2.17, 2.10, 2.02 (3s, each 3H, 2×OAc), 1.51, 1.36 (2s, each 3H, CMe$_2$).
elementary analysis as C$_{16}$H$_{25}$NO$_8$ (%): C: 53.47, H: 7.01, N: 3.90 (calculated). C: 53.21, H: 6.98, N: 3.76 (found).
$[\alpha]_D^{20}$: −7.0° (c, 0.30, CHCl$_3$).

d) Compound 51 (30 mg, 0.083 mmol) after being mixed with 80% acetic acid (1 ml) was stirred in an oil bath at 60° C. for 12 hours. A residue (24 mg) was obtained by azeotropically concentrating the reaction liquid in vacuo and with toluene. The residue, on addition of pyridine (0.5 ml) and acetic anhydride (0.5 ml), was eventually reacted with stirring at room temperature for 4 hours and azeotropically concentrated in vacuo and with toluene. The residue was silica gel-chromatographed (ethanol/toluene=⅛) to provide as a syrup title compound 52 or ultimate compound L (33 mg, 98% yield).

compound 52 (compound L)

Rf: 0.35 (ethanol/toluene=1/6, v/v).
mp: syrup.
IR (neat): 3400 cm$^{-1}$ (NH), 1750 cm$^{-1}$ (OAc), 1670 cm$^{-1}$ (amide), 1520 cm$^{-1}$ (amide).
$^1$H-NMR ($\delta$, 90 MHz, CDCl$_3$): 6.10 (d, 1H, $J_{2,NH}$=9.0 Hz, NH), 5.52–5.00 (m, 4H, H-1, 4, 5, 6), 5.00–4.70 (m, 1H, H-2), 3.78 (t, 1H, J=3.0 Hz, J=3.5 Hz), 3.40 (s, 3H, OMe), 2.16, 2.07, 2.03 (3s, 3H, 6H, 3H, NHAc, 3×OAc).
elementary analysis as C$_{17}$H$_{25}$NO$_{10}$ (%): C: 50.62, H: 6.25, N: 3.47 (calculated). C: 50.34, H: 6.31, N: 3.34 (found).
$[\alpha]_D^{20}$: +8.5° (c, 1.17, CHCl$_3$).

e) Compound 9 was converted, through the reaction route of Example 2, to compound A.

EXAMPLE 9

1D-1-acetamido-2,3,4,6-tetra-O-acetyl-1-deoxy-5-O-methyl-neo-inositol (compound 58) (compound M)

a) To compound 7 (3.94 g, 10.1 mmol) were added pyridine (7 ml) and acetic anhydride (7 ml), and reaction was made with stirring at room temperature for 16 hours. Into the reaction liquid were incorporated with ice cooling methanol and then toluene, the mixture being allowed to undergo azeotropic concentration in vacuo and with toluene. After being diluted with ethyl acetate, the residue was washed with hydrochloric acid (250 ml, 1M), aqueous sodium bicarbonate (250 ml, saturated) and aqueous sodium chloride (250 ml, saturated) in the order mentioned. The resulting organic phase, on drying with sodium sulfate anhydride, was filtered to remove that agent, followed by azeotropic concentration in vacuo and with toluene. Silica gel chromatographing (ethyl acetate/toluene=1/10) of the residue gave 1L-1,4,5,6-tetra-O-acetyl-2-O-methyl-3-O-(p-toluenesulfonyl)-chiro-inositol (compound 53) (4.03 g, 77% yield).

compound 53

Rf: 0.85 (toluene/ethyl acetate=⅛, v/v).
mp: syrup.
IR (neat): 1750 cm$^{-1}$ (OAc), 1175 cm$^{-1}$ (SO$_2$).
$^1$H-NMR ($\delta$, 90 MHz, CDCl$_3$): 7.78, 7.33 (2d, each 2H, J=9.0 Hz, SO$_2$), 5.61–5.11 (m, 4H, H-1, 4, 5, 6), 4.92 (t, 1H, $J_{2,3}$=$J_{3,4}$=9.7 Hz, H-3), 3.51 (dd, 1H, $J_{1,2}$=3.4 Hz, H-2), 3.06 (s, 3H, OMe), 2.16, 2.11, 2.07, 1.98 (4s, each 3H, 4×OAc).
elementary analysis as C$_{22}$H$_{28}$O$_{12}$S (%): C: 51.16, H: 5.46 (calculated). C: 51 15, H: 5.65 (found).
$[\alpha]_D^{19}$: −9.9° (c, 1.15, CHCl$_3$).

b) To compound 53 (412 mg, 0.798 mmol) were added sodium azide (284 mg, 4.37 mmol) and aqueous 90% 2-methoxyethanol (4 ml). Reaction was made with refluxing in an oil bath at 120° C. for 10 hours. From azeotropic concentration of the reaction liquid in vacuo and with toluene, a brown solid was derived which, after addition of pyridine (5 ml) and acetic anhydride (5 ml), was stirred at room temperature for 4 hours. Conducted after completion of the reaction were concentration by toluene azeotropy in vacuum and washing with distilled water (twice each 20 ml).

The resulting organic phase was dried with sodium sulfate anhydride and filtered to remove that agent. Toluene-azeotropy, vacuum-concentration of the filtrate gave a syrupy mixture (300 mg) of compounds 54, 55 and 56. By silica gel chromatography (hexane/ethyl acetate=3/1), the mixture was purified to separately obtain 1L-2,3,4,6-tetra-O-acetyl-1-azido-1-deoxy-5-O-methyl-neo-inositol (compound 54) (94 mg, 30% yield), 1L-1,4,5,6-tetra-O-acetyl-2-azido-2-deoxy-3-O-methyl-chiro-inositol (compound 55) (92 mg, 30% yield) and 1D-1,4,5,6-tetra-O-acetyl-2-azido-2-deoxy-3-O-methyl-allo-inositol (compound 56) (16 mg, 5% yield).

compound 54

Rf: 0.47 (hexane/ethyl acetate=2/1, v/v).
mp: 105°–107° C. (ethanol).
IR (neat): 2110 cm$^{-1}$ (N$_3$), 1750 cm$^{-1}$ (OAc),
$^1$H-NMR ($\delta$, 90 MHz, CDCl$_3$): 5.62 (t, 1H, $J_{1,2}$=$J_{2,3}$=2.5 Hz, H-2), 5.40–5.05 (m, 3H, H-3, 4, 6), 4.03 (dd, 1H, $J_{1,6}$=11.0 Hz, H-4), 3.96 (t, 1H, $J_{4,5}$=$J_{5,6}$=2.5 Hz, H-5), 3.51 (s, 3H, OMe), 2.18, 2.14, 2.07, 1.98 (4s, each 3H, 4×OAc).

elementary analysis as $C_{15}H_{21}N_3O_9$ (%): C: 46.51, H: 5.46, N: 10.84 (calculated). C: 46.70, H: 5.31, N: 10.73 (found).

$[\alpha]_D^{19}$: +129.5° (c, 0.80, $CHCl_3$).

compound 55

Rf: 0.50 (hexane/ethyl acetate=2/1, v/v).
mp: syrup.
IR (neat): 2100 $cm^{-1}$ ($N_3$), 1760 $cm^{-1}$ (OAc),
$^1$H-NMR ($\delta$, 90 MHz, $CDCl_3$): 5.55-5.00 (m, 4H, H-1, 4, 5, 6), 3.90-3.48 (m, 2H, H-2, 3), 3.45 (s, 3H, OMe), 2.17, 2.15, 2.11, 1.98 (4s, each 3H, 4×OAc).

elementary analysis as $C_{15}H_{21}N_3O_9$ (%): C: 46.51, H: 5.46, N: 10.84 (calculated). C: 46.39, H: 5.28, N: 10.85 (found).

$[\alpha]_D^{19}$: −4.1° (c, 1.04, $CHCl_3$).

compound 56

Rf: 0.30 (hexane/ethyl acetate=2/1, v/v).
mp: 175°-176° C. (ethanol).
IR (neat): 2100 $cm^{-1}$ ($N_3$), 1750 $cm^{-1}$ (OAc),
$^1$H-NMR ($\delta$, 90 MHz, $CDCl_3$): 5.55-5.05 (m, 4H, H-1, 4, 5, 6), 4.30-4.12 (m, 1H, H-2), 3.80 (t, 1H, $J_{2,3}=J_{3,4}=3.5$ Hz, H-3), 3.47 (s, 3H, OMe), 2.19, 2.14, 2.09, 2.01 (4s, each 3H, 4×OAc).

elementary analysis as $C_{15}H_{21}N_3O_9$ (%): C: 46.51, H: 5.46, N: 10.84 (calculated). C: 46.15, H: 5.33, N: 10.70 (found).

$[\alpha]_D^{19}$: +24.7° (c, 0.80, $CHCl_3$).

c) Compound 54 (35 mg, 0.09 mmol) was reacted, with addition of ethanol (1 ml), acetic anhydride (0.1 ml) and Raney nickel-T4 catalyst (an amount of one small spatula), with stirring in a hydrogen atmosphere at one atm for 1.5 hours. Residual catalyst was subsequently removed by filtration. By silica gel chromatography (ethanol/toluene=⅛), the filtrate was purified to provide as a white solid title compound 58 or ultimate compound M (32 mg, 88% yield).

compound 58 (compound M)

Rf: 0.37 (ethanol/toluene=1/5, v/v).
mp: 270°-280° C. (ethanol).
IR (neat): 3260 $cm^{-1}$ (NH), 1750 $cm^{-1}$ (OAc), 1650 $cm^{-1}$ (amide), 1560 $cm^{-1}$ (amide).
$^1$H-NMR ($\delta$, 90 MHz, $CDCl_3$): 5.60 (d, 1H, $J_{1,NH}=9.0$ Hz, NH), 5.50 (t, 1H, $J_{1,2}=J_{2,3}=3.0$ Hz, H-2), 5.40 (dd, 1H, $J_{3,4}=10.0$ Hz, H-3), 5.15 (dd, 1H, $J_{1,6}=12.0$ Hz, $J_{5,6}=3.0$ Hz, H-6), 5.08 (dd, 1H, $J_{4,5}=3.0$ Hz, H-4), 4.76 (ddd, 1H, H-1), 3.86 (t, 1H, H-5), 3.54 (s, 3H, OMe), 2.16, 2.10, 1.95, 1.90 (4s, 3H, 6H, 3H, 3H, NHAc, 4×OAc).

elementary analysis as $C_{17}H_{25}NO_{10}$ (%): C: 50.62, H: 6.25, N: 3.47 (calculated). C: 50.53, H: 6.15, N: 3.47 (found).

$[\alpha]_D^{20}$: +2.7° (c, 0.49, $CHCl_3$).

d) Compound 56 (9.7 mg, 0.025 mmol) was incorporated with ethanol (0.5 ml), acetic anhydride (0.1 ml) and Raney nickel-T4 catalyst (an amount of one small spatula). The mixture was stirred in a hydrogen atmosphere at one atm for 4 hours. After being filtered to remove residual catalyst, the reaction liquid was azeotropically concentrated in vacuo and with toluene to thereby form a pale-yellow, crystal-like residue (19 mg). Purification by silica gel chromatography (ethanol/toluene=⅛) provided compound L (8.4 mg, 83% yield). The compound thus produced was identified by TLC, $^1$H-NMR and IR analyses.

EXAMPLE 9-1 (REFERENCE)

compound 12 (compound A) from compound 55

Compound 55 was reacted with stirring in a hydrogen atmosphere with addition of ethanol, acetic anhydride and Raney nickel-T4 catalyst. Similar subsequent treatments gave compound A.

EXAMPLE 10

1D-3-acetamido-1,2,4,5-tetra-O-acetyl-3-deoxy-6-O-methyl-chiro-inositol (compound 62) (compound N)

a) Compound 16 (2.90 g, 7.431 nmol) obtained in items a) and b) of Example 1 was incorporated with pyridine (6 ml) and acetic anhydride (6 ml). Reaction was made with stirring at room temperature for 15 hours. The reaction liquid was azeotropically concentrated in vacuo and with toluene, followed by dilution with ethyl acetate (200 ml) and by subsequent washing with hydrochloric acid (200 ml, 1M), aqueous sodium bicarbonate (200 ml, saturated) and aqueous sodium chloride (200 ml, saturated) in this order. The resulting organic phase after being dried with sodium sulfate anhydride was filtered to remove that agent. On toluene-azeotropy, vacuum-concentration of the filtrate, the residue was silica gel-chromatographed (ethyl acetate/toluene=⅛) to obtain 1L-1,3,5,6-tetra-O-acetyl-2-O-methyl-4-O-(p-toluenesulfonyl)-chiro-inositol (compound 59) (3.68 g, 96% yield).

compound 59

Rf: 0.77 (toluene/ethyl acetate=5/1, v/v).
mp: 129°-131° C. (ethanol).
IR (neat): 1775 $cm^{-1}$ (OAc), 1175 $cm^{-1}$ ($SO_2$).
$^1$H-NMR ($\delta$, 90 MHz, $CDCl_3$): 7.70, 7.28 (2d, each 2H, J=9.0 Hz, $SO_2PhMe$), 5.51-5.13 (m, 4H, H-1, 3, 5, 6), 5.02 (t, 1H, $J_{3,4}=J_{4,5}=9.4$ Hz, H-4), 3.58 (dd, 1H, $J_{1,2}=2.5$ Hz, $J_{2,3}=9.4$ Hz, H-2), 3.38 (s, 3H, OMe), 2.44 (s, 3H, PhMe), 2.21, 2.16, 2.04, 1.89 (4s, each 3H, 4×OAc).

elementary analysis as $C_{22}H_{28}O_{12}S$ (%): C: 51.16, H: 5.46 (calculated). C: 51.23, H: 5.08 (found).

$[\alpha]_D^{23}$: −16.6° (c, 1.23, $CHCl_3$).

c) Compound 59 (700 mg, 1.36 mmol) was incorporated with sodium azide (480 mg, 7.38 mmol) and aqueous 90% 2-methoxyethanol (7 ml), and the mixture was refluxed in an oil bath at 120° C. for 20 hours. A brown solid (1.11 g) was derived by azeotropically concentrating the reaction liquid in vacuo and with toluene. With pyridine (5 ml) and acetic anhydride (5 ml) added to the solid, reaction was made with stirring at room temperature for 2.5 hours. After similar azeotropic concentration, the resulting residue was diluted with ethyl acetate (150 ml) and washed with distilled water (twice each 50 ml).

The organic layer thus obtained was dried with sodium sulfate anhydride and then filtered to remove the drying agent. Toluene-azeotropy, vacuum-concentration gave a syrupy mixture (600 mg) of compounds 60 and 61. By silica gel chromatography (toluene/ethyl acetae=6/1), the mixture was purified to form 1D-1,2,4,5-tetra-O-acetyl-3-azido-3-deoxy-6-O-methyl-chiro-inositol (compound 60) (392 mg, 73% yield) and 1D-1,2,4,6-tetra-O-acetyl-3-azido-3-deoxy-5-O-methyl-chiro-inositol (compound 61) (84 mg, 15.6% yield).

compound 60

Rf: 0.33 (toluene/ethyl acetate=4/1, v/v).

mp: 91°-93° C. (ethanol).

IR (neat): 2110 cm$^{-1}$ (N$_3$), 1755 cm$^{-1}$ (OAc).

$^1$H-NMR ($\delta$, 90 MHz, CDCl$_3$): 5.52 (dd, 1H, J$_{1,2}$=4.0 Hz, J$_{1,6}$=3.0 Hz, H-1), 5.36 (dd, 1H, J$_{3,4}$=9.0 Hz, J$_{4,5}$=10.0 Hz, H-4), 5.14 (dd, 2H, J$_{5,6}$=4.0 Hz, J$_{2,3}$=10.0 Hz, H-2, 5), 3.34 (dd, 1H, H-3), 3.17 (dd, 1H, H-6), 3.50 (s, 3H, OMe), 2.16, 2.10, 2.08, (3s, 3H, 3H, 6H, 4×OAc).

elementary analysis as C$_{15}$H$_{21}$N$_3$O$_9$ (%): C: 46.51, H: 5.46, N: 10.84 (calculated). C: 46.41, H: 5.27, N: 10.79 (found).

[$\alpha$]$_D^{19}$: +13.7° (c, 1.07, CHCl$_3$).

compound 61

Rf: 0.27 (toluene/ethyl acetate=4/1, v/v).
mp: 102°-103° C. (ethanol).

IR (neat): 2110 cm$^{-1}$ (N$_3$), 1755 cm$^{-1}$ (AcO).

$^1$H-NMR ($\delta$, 90 MHz, CDCl$_3$): 5.48 (t, 2H, J$_{1,2}$=J$_{1,6}$=J$_{5,6}$=3.0 Hz, H-1, 6), 5.18 (t, J$_{2,3}$=J$_{3,4}$=10.0 Hz, H-3), 5.07 (dd, 1H, J$_{4,5}$=10.0 Hz, H-5), 3.80 (t, 1H, H-4), 3.50 (dd, 1H, H-2), 3.33 (s, 3H, OMe), 2.18, 2.17, 2.07 (3s, 3H, 6H, 3H, 4×OAc).

elementary analysis as C$_{15}$H$_{31}$N$_3$O$_9$ (%): C: 46.51, H: 5.46, N: 10.84 (calculated). C: 46.49, H: 5.31, N: 10.88 (found).

[$\alpha$]$_D^{10}$: +10.7° (c, 0.34, CHCl$_3$).

d) To compound 60 (105 mg, 0.271 mmol) were added ethanol (1 ml), acetic anhydride (0.15 ml) and Raney nickel-T4 catalyst (an amount of three small spatulas). Reaction was made with stirring in a hydrogen atmosphere at one atm for 4 hours. After removal of residual catalyst by filtration, silica gel-chromatographing of the filtrate provided as a white solid title compound 62 or ultimate compound N (100 mg, 91% yield).

compound 62 (compound N)

Rf: 0.39 (ethanol/toluene=⅛, v/v).
mp: 144°-145° C. (ethanol).

IR (neat): 3360 cm$^{-1}$ (NH), 3280 cm$^{-1}$ (NH), 1750 cm$^{-1}$ (OAc), 1670 cm$^{-1}$ (amide), 1550 cm$^{-1}$ (amide).

$^1$H-NMR ($\delta$, 90 MHz, CDCl$_3$): 5.04 (d, 1H, J$_{3,NH}$=10.0 Hz, NHAc), 5.01 (dd, 1H, J$_{1,2}$=3.0 Hz, J$_{1,6}$=4.0 Hz, H-1), 5.30-5.10 (m, 3H, H-2, 4, 5), 4.75-4.35 (m, 1H, H-3), 3.72 (dd, 1H, J$_{5,6}$=2.0 Hz, H-6), 3.49 (s, 3H, OMe), 2.36, 2.15, 2.07, 2.04, 1.90 (5s, each 3H, 4×OAc, NHAc).

elementary analysis as C$_{17}$H$_{25}$NO$_{10}$ (%): C: 5062, H: 6.25, N: 3.47 (calculated). C: 50.67, H: 6.12, N: 3.44 (found).

[$\alpha$]$_D^{19}$: +14.6° (c, 1.28, CHCl$_3$).

EXAMPLE 10-1 (REFERENCE)

compound 21 (compound B) from compound 61

To compound 61 were added ethanol (1 ml), acetic anhydride (0.1 ml),and Raney nickel-T4 catalyst (an amount of one small spatula). Reaction was made with stirring in a hydrogen atmosphere at one atm for 5 hours. Residual catalyst was removed by filtration. By silica gel chromatography (ethanol/toluene=1/10), the filtrate was purified to provide compound B (32 mg, 85.3 % yield).

EXAMPLE 11

1L-1-acetamido-2,3,4,5-tetra-O-acetyl-1-deoxy-6-O-methyl-myo-inositol (compound 67),(compound O)

a) To compound 3 (206 mg, 0.751 mmol) were added p-toluenesulfonyl chloride (716 mg, 3.75 mmol) and pyridine (5 ml). The mixture was stirred in an oil bath at 60° C. for 23 hours. Ethyl acetate (70 ml) was incorporated to dilute the reaction liquid which was thereafter was washed with distilled water (three times each 20 ml). The resulting organic phase after being dried with sodium sulfate anhydride was filtered to remove that agent. Subsequent azeotropic concentration in vacuo and with toluene gave a pale-yellow, oil-like residue. By silica gel chromatography (hexane/ethyl acetate=6/1 plus triethylamine 1%), the residue was purified to obtain 1L-1,2:3,4-di-O-isopropylidene-5-O-methyl-6-O-(p-toluenesulfonyl)-chiro-inositol (compound 63),(317 mg, 99% yield).

compound 63

Rf: 0.31 (hexane/ethyl acetate=4/1, v/v).
mp: syrup.

IR (neat): 1175 cm$^{-1}$ (SO$_2$).

$^1$H-NMR ($\delta$, 90 MHz, CDCl$_3$): 7.83, 7.34 (2d, each 2H, J=8.0 Hz, SO$_2$ PhMe), 5.03 (t, 1H, J$_{1,6}$=J$_{5,6}$=3.5 Hz, H-6), 4.50-4.20 (m, 2H, H-1, 2), 3.75-3.50 (m, 3H, H-3, 4, 5), 3.25 (s, 3H, OMe), 2.44 (s, 3H, SO$_2$ PhMe), 1.42, 1.38, 1.30 (3s, 6H, 3H, 3H, 2×CMe$_2$).

elementary analysis as C$_{20}$H$_{28}$O$_8$S (%): C:56.06, H: 6.59 (calculated). C: 55.89, H: 6.51 (found).

[$\alpha$]$_D^{22}$: −14.0° (c, 1.43, CHCl$_3$).

b) Compound 63 (120 mg, 0.28 mmol) after being incorporated with sodium azide (91 mg, 1.40 mmol) and DMSO (1 ml) was stirred in an oil bath at 120° C. for 19 hours. The reaction liquid was diluted with ethyl acetate (60 ml) and then washed with distilled water (twice each 20 ml). Sodium sulfate anhydride was put into the resulting organic phase and, after drying, removed by filtration. A residue (82 mg) was obtained by azeotropically concentrating the filtrate in vacuo and with toluene. Subsequent purification by silica gel chromatography (toluene/ethyl acetate=12/1 plus triethylamine 1%) gave 1L-1-azido-1-deoxy-2,3:4,5-di-O-isopropylidene-6-O-methyl-myo-inositol (compound 64),(59 mg, 71% yield) and (1S, 4R, 8S, 9R)-2-methoxy-6,6,11,11-tetramethyl-5,7,10-12-tetraoxa-tricyclo[7,3,0,0$^{4,8}$]dodec-2-ene (compound 65),(12 mg, 17% yield).

compound 64

Rf: 0.48 (toluene/ethyl acetate=5/1, v/v).
mp: syrup.

IR (neat): 2100 cm$^{-1}$ (N$_3$).

$^1$H-NMR ($\delta$, 90 MHz, CDCl$_3$): 4.60-3.25 (m, 6H, H-1, 2, 3, 4, 5, 6), 3.53 (s, 3H, OMe), 1.59, 1.46, 1.40 (3s, 3H, 6H, 3H, 2×CMe$_2$).

elementary analysis as C$_{13}$H$_{21}$N$_3$O$_5$ (%):
C: 52.16, H: 7.07, N: 14.04 (calculated).
C: 52.39, H: 6.91, N: 13.78 (found).

[$\alpha$]$_D^{19}$: +47.8° (c, 1.12, CHCl$_3$).

compound 65

Rf: 0.42 (toluene/ethyl acetate=5/1, v/v).
mp: 70°-73° C.

IR (neat): 1645 cm$^{-1}$ (C=C).

$^1$H-NMR ($\delta$, 90 MHz, CDCl$_3$): 4.95 (ddd, 1H, J$_{1,4}$=1.0 Hz, J$_{3,4}$=4.0 Hz, J$_{4,8}$=7.0 Hz, H-4), 4.66 (dd, 1H, J$_{1,3}$=2.0 Hz, H-3), 4.46 (dd, 1H, J$_{8,9}$=9.5 Hz, H-8), 4.14 (ddd, 1H, J$_{1,9}$=9.5 Hz, H-1), 3.82 (t, 1H, H-9), 3.67 (s, 3H, OMe), 1.54, 1.50, 1.47, 1.40 (4s, each 3H, 2×CMe$_2$).

elementary analysis as C$_{13}$H$_{20}$O$_5$ (%): C: 60.94, H: 7.81 (calculated). C: 60.69, H: 7.64 (found).

$[\alpha]_D^{20}$: −7.8° (c, 0.5, CHCl$_3$).

c) To compound 64 (60 mg, 0.20 mmol) were added ethanol (0.5 ml) and hydrochloric acid (1 ml, 2M), and reaction was made with stirring in an oil bath at 60° C. for one hour. A residue (46 mg) was derived from vacuum concentration of the reaction liquid by azeotropy with ethanol and then toluene. With pyridine (2 ml) and acetic anhydride (2 ml) added to that residue, stirring was done at room temperature for 2 hours. Conducted after completion of the reaction were dilution with ethyl acetate (40 ml) and washing with distilled water (three times each 5 ml).

The resulting organic phase was dried with sodium sulfate anhydride, followed by filtration to remove the drying agent and by subsequent azeotropic concentration of the filtrate in vacuo and with toluene. The residue (104 mg) thus derived was silica gel-chromatographed (toluene/ethyl acetate=8/1),to obtain 1L-2,3,4,5-tetra-O-acetyl-1-azido-1-deoxy-6-O-methyl-myo-inositol (compound 66) (77 mg, 99% yield).

compound 66

Rf: 0.48 (toluene/ethyl acetate=5/1, v/v).
mp: 174.0°–174.5° C. (ethanol).
IR (neat): 2100 cm$^{-1}$ (N$_3$), 1760 cm$^{-1}$ (OAc).
$^1$H-NMR ($\delta$, 90 MHz, CDCl$_3$): 5.55 (t, 1H, J$_{1,2}$=J$_{2,3}$=2.5 Hz, H-2), 5.47 (t, 1H, J$_{3,4}$=J$_{4,5}$=10.0 Hz, H-4), 5.10 (m, 1H, H-5), 4.91 (dd, 1H, H-3), 3.87–3.31 (m, 2H, H-1, 6), 3.57 (s, 3H, OMe), 2.19, 2.11, 2.02, 1.98 (4s, each 3H, 3×OAc).

elementary analysis as C$_{15}$H$_{21}$N$_3$O$_9$ (%): C: 46.51, H: 5.46, N: 10.84 (calculated). C: 46.24, H: 5.37, N: 10.81 (found).

$[\alpha]_D^{22}$: −39° (c, 1.175, CHCl$_3$).

d) Compound 66 (68 mg, 0.18 mmol) after being incorporated with ethanol (1 ml), acetic anhydride (0.1 ml) and Raney nickel-T4 catalyst (an amount of two small spatulas) was stirred in a hydrogen atmosphere at one atm for 3.5 hours. Residual catalyst was removed by filtration. By silica gel chromatography (ethanol/toluene=⅛), the filtrate was purified to provide as a white solid title compound 67 or ultimate compound O.

compound 67 (Compound O)

Rf: 0.36 (ethanol/toluene=1/6, v/v).
mp: 189°–190° C. (ethanol).
IR (neat): 3300 cm$^{-1}$ (NH), 1750 cm$^{-1}$ (OAc), 1650 cm$^{-1}$ (amide), 1550 cm$^{-1}$ (amide).
$^1$H-NMR ($\delta$, 90 MHz, CDCl$_3$): 5.75–5.45 (m, 1H, NH), 5.53 (t, 1H, J$_{1,2}$=J$_{2,3}$=3.0 Hz, H-2), 5.59 (m, 2H, J$_{3,4}$=J$_{4,5}$=J$_{5,6}$=9.0 Hz, H-4, 5), 5.02 (dd, 1H, H-6), 3.45 (s, 3H, OMe), 2.18, 2.08, 2.01, 1.99, 1.95 (5s, each 3H, 4×OAc, NHAc).

elementary analysis as C$_{17}$H$_{25}$NO$_{10}$ (%): C: 50.62, H: 6.25, N: 3.47 (calculated). C: 50.67, H: 6.11, N: 3.45 (found).

$[\alpha]_D^{20}$: +8.9° (c, 0.94, CHCl$_3$).

What is claimed is:

1. An inositol compound having stereospecific structure and optical activity selected from the group consisting of 1L-3-acetamido-1,4,5,6-tetra-O-acetyl-3-deoxy-2-O-methyl-chiro-inositol of the formula

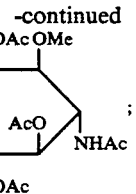

(I)

1L-3-acetamido-1,2,4,6-tetra-O-acetyl-3-deoxy-5-O-methyl-chiro-inositol of the formula

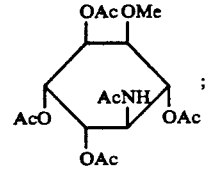

(II)

1D-2-acetamido-1,3,4,5-tetra-O-acetyl-2-deoxy-6-O-methyl-chiro-inositol of the formula

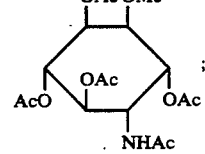

(III)

1L-2-acetamido-1,3,4,6-tetra-O-acetyl-2-deoxy-5-O-methyl-chiro-inositol of the formula

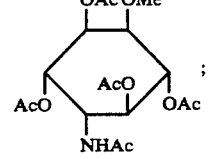

(IV)

1D-2,4-diacetamido-1,3,5-tri-O-acetyl-2,4-dideoxy-6-O-methyl-chiro-inositol of the formula

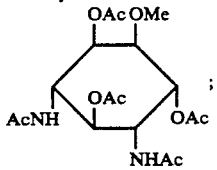

(V)

1D-1,2-diacetamido-4,5,6-tri-O-acetyl-1,2-dideoxy-3-O-methyl-chiro-inositol of the formula

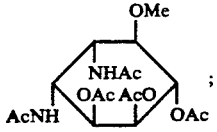

(VI)

1L-3-acetamido-1,2,4,6-tetra-O-acetyl-3-deoxy-5-O-methyl-muco-inositol of the formula

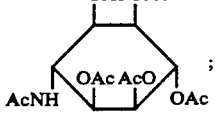

(VII)

1L-1-acetamido-2,3,4,6-tetra-O-acetyl-3-deoxy-5-O-methyl-chiro-inositol of the formula

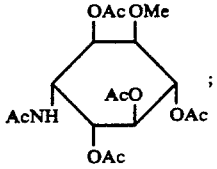

(VIII)

1D-1-acetamido-3,4,5,6-tetra-O-acetyl-1-deoxy-

-continued

2-O-methyl-scyllo-inositol of the formula

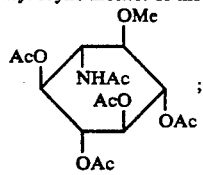 (IX)

1L-1-acetamido-3,4,5,6-tetra-O-acetyl-1-deoxy-
2-O-methyl-chiro-inositol of the formula

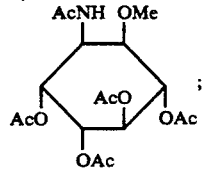 (X)

1L-1-acetamido-2,4,5,6-tetra-O-acetyl-1-deoxy-
3-O-methyl-scyllo-inositol of the formula

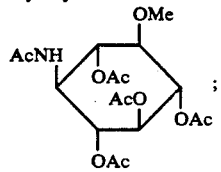 (XI)

1D-2-acetamido-1,4,5,6-tetra-O-acetyl-2-deoxy-
3-O-methyl-allo-inositol of the formula

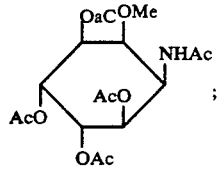 (XII)

1D-1-acetamido-2,3,4,6-tetra-O-acetyl-1-deoxy-
5-O-methyl-neo-inositol of the formula

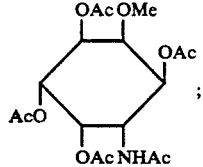 (XIII)

1D-3-acetamido-1,2,4,5-tetra-O-acetyl-3-deoxy-
6-O-methyl-chiro-inositol of the formula

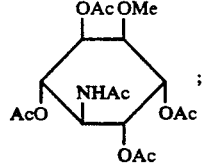 (XIV)

and 1L-1-acetamido-2,3,4,5-tetra-O-acetyl-1-deoxy-
6-O-methyl-myo-inositol of the formula

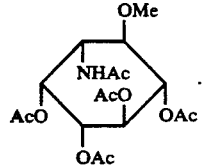 (XV)

2. The compound of claim 1 which is 1L-3-acetamido-1,4,5,6-tetra-O-acetyl-3-deoxy-2-O-methyl-chiro-inositol of formula (I)

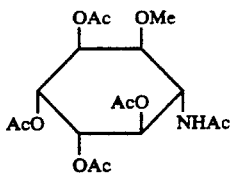 (I)

3. The compound of claim 1 which is 1L-3-acetamido-1,2,4,6-tetra-O-acetyl-3-deoxy-5-O-methyl-chiro-inositol of formula (II)

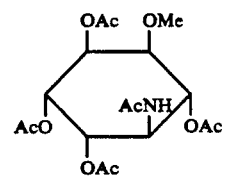 (II)

4. The compound of claim 1 which is 1D-2-acetamido-1,3,4,5-tetra-O-acetyl-2-deoxy-6-O-methyl-chiro-inositol of formula (III)

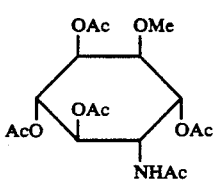 (III)

5. The compound of claim 1 which is 1L-2-acetamido-1,3,4,6-tetra-O-acetyl-2-deoxy-5-O-methyl-chiro-inositol of formula (IV)

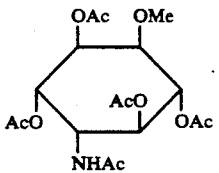 (IV)

6. The compound of claim 1 which is 1D-2,4-diacetamido-1,3,5-tri-O-acetyl-2,4-dideoxy-6-O-methyl-chiro-inositol of formula (V)

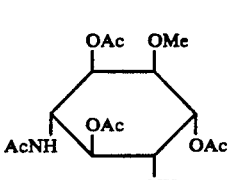 (V)

7. The compound of claim 1 which is 1D-1,2-diacetamido-4,5,6-tri-O-acetyl-1,2-dideoxy-3-O-methyl-chiro-inositol of formula (VI)

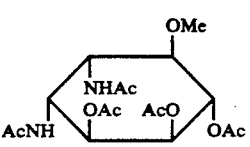 (VI)

8. The compound of claim 1 which is 1L-3-acetamido-1,2,4,6-tetra-O-acetyl-3-deoxy-5-O-methyl-muco-inositol of formula (VII)

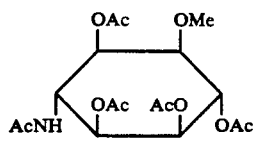
(VII)

9. The compound of claim 1 which is 1L-1-acetamido-2,3,4,6-tetra-O-acetyl-1-deoxy-5O-methyl-chiro-inositol of formula (VIII)

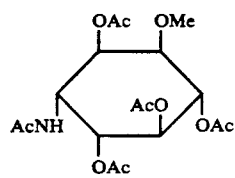
(VIII)

10. The compound of claim 1 which is 1D-1-acetamido-3,4,5,6-tetra-O-acetyl-1-deoxy-2-O-methyl-scyllo-inositol of formula (IX)

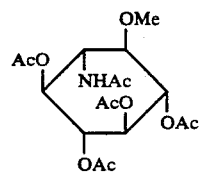
(IX)

11. The compound of claim 1 which is 1L-1-acetamido-3,4,5,6-tetra-O-acetyl-1-deoxy-2-O-methyl-chiro-inositol of formula (X)

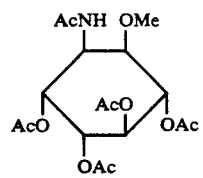
(X)

12. The compound of claim 1 which is 1L-1-acetamido-2,4,5,6-tetra-O-acetyl-1-deoxy-3-O-methyl-scyllo-inositol of formula (XI)

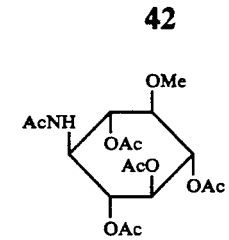
(XI)

13. The compound of claim 1 which is 1D-2-acetamido-1,4,5,6-tetra-O-acetyl-2-deoxy-3-O-methyl-allo-inositol of formula (XII)

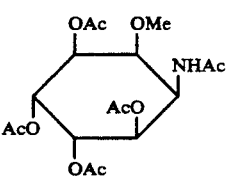
(XII)

14. The compound of claim 1 which is 1D-1-acetamido-2,3,4,6-tetra-O-acetyl-1-deoxy-5-O-methyl-neo-inositol of formula (XIII)

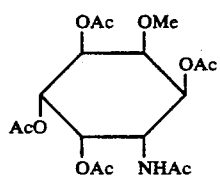
(XIII)

15. The compound of claim 1 which is 1D-3-acetamido-1,2,4,5-tetra-O-acetyl-3-deoxy-6-O-methyl-chiro-inositol of formula (XIV)

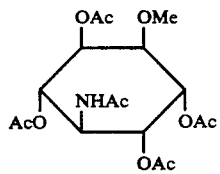
(XIV)

16. The compound of claim 1 which is 1L-1-acetamido-2,3,4,5-tetra-O-acetyl-1-deoxy-6-O-methyl-myo-inositol of formula (XV)

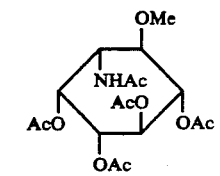
(XV)

* * * * *